United States Patent
Raiszadeh et al.

(10) Patent No.: US 12,016,783 B2
(45) Date of Patent: *Jun. 25, 2024

(54) IMPLANTS AND METHODS FOR SPINAL FUSION

(71) Applicant: NuVasive, Inc., San Diego, CA (US)

(72) Inventors: Kamshad Raiszadeh, San Diego, CA (US); Benjamin VerHage, San Francisco, CA (US); Michael Mindoro, Dublin, CA (US); Jared Arambula, San Diego, CA (US); Dan K. Ahlgren, San Diego, CA (US); Michael C. Di Lauro, Carlsbad, CA (US)

(73) Assignee: Nuvasive, Inc., San Diego, CA (US)

( * ) Notice: Subject to any disclaimer, the term of this patent is extended or adjusted under 35 U.S.C. 154(b) by 738 days.

This patent is subject to a terminal disclaimer.

(21) Appl. No.: 17/073,891

(22) Filed: Oct. 19, 2020

(65) Prior Publication Data

US 2021/0030558 A1 Feb. 4, 2021

Related U.S. Application Data

(63) Continuation of application No. 15/906,534, filed on Feb. 27, 2018, now Pat. No. 10,842,646, which is a (Continued)

(51) Int. Cl.
*A61F 2/44* (2006.01)
*A61F 2/46* (2006.01)
(Continued)

(52) U.S. Cl.
CPC .............. *A61F 2/447* (2013.01); *A61F 2/442* (2013.01); *A61F 2/4611* (2013.01);
(Continued)

(58) Field of Classification Search
CPC ......... A61F 2/447; A61F 2/442; A61F 2/4611
See application file for complete search history.

(56) References Cited

U.S. PATENT DOCUMENTS

| 3,486,505 A | 12/1969 | Morrison |
|---|---|---|
| 3,518,993 A | 7/1970 | Blake |

(Continued)

FOREIGN PATENT DOCUMENTS

| CA | 2015507 C | 1/1999 |
|---|---|---|
| EP | 0369603 A1 | 5/1990 |

(Continued)

OTHER PUBLICATIONS

Alleyne et al., "Current and future approaches to lumbar disc surgery: A literature review", MedGenMed, 1999, 1, No. 1.

(Continued)

*Primary Examiner* — Ellen C Hammond

(57) ABSTRACT

An implant is provided for performing spinal fusion. The implant includes an implant body having a leading side and a trailing side at opposing ends along a longitudinal axis. Between the leading side and trailing side are an upper surface, a lower surface, an anterior side, and a posterior side. At least one keel structure is provided extending from the implant body for penetration into an adjacent vertebral body. A trial sizer and keel cutter may be utilized to form keel channels within the vertebral body to receive the keel structure.

18 Claims, 24 Drawing Sheets

Related U.S. Application Data continuation of application No. 14/924,490, filed on Oct. 27, 2015, now Pat. No. 9,907,672, which is a continuation of application No. 13/337,967, filed on Dec. 27, 2011, now Pat. No. 9,168,152, which is a continuation of application No. 12/380,693, filed on Mar. 2, 2009, now Pat. No. 8,083,796.

(60) Provisional application No. 61/067,700, filed on Feb. 29, 2008, provisional application No. 61/105,796, filed on Oct. 15, 2008.

(51) Int. Cl.
*A61F 2/28* (2006.01)
*A61F 2/30* (2006.01)

(52) U.S. Cl.
CPC .............. *A61F 2002/2817* (2013.01); *A61F 2002/2835* (2013.01); *A61F 2002/3008* (2013.01); *A61F 2002/30477* (2013.01); *A61F 2002/30578* (2013.01); *A61F 2002/30593* (2013.01); *A61F 2002/30604* (2013.01); *A61F 2002/30774* (2013.01); *A61F 2002/30785* (2013.01); *A61F 2002/3082* (2013.01); *A61F 2002/30841* (2013.01); *A61F 2002/30878* (2013.01); *A61F 2002/30904* (2013.01); *A61F 2/4603* (2013.01); *A61F 2002/4629* (2013.01); *A61F 2/4684* (2013.01); *A61F 2220/0008* (2013.01); *A61F 2230/0019* (2013.01); *A61F 2310/00023* (2013.01); *A61F 2310/00976* (2013.01)

(56) References Cited

U.S. PATENT DOCUMENTS

| | | |
|---|---|---|
| 3,604,487 A | 9/1971 | Gilbert |
| 3,745,995 A | 7/1973 | Kraus |
| 3,848,601 A | 11/1974 | Ma et al. |
| 3,867,728 A | 2/1975 | Stubstad et al. |
| 4,026,304 A | 5/1977 | Levy |
| 4,026,305 A | 5/1977 | Brownlee et al. |
| 4,349,921 A | 9/1982 | Kuntz |
| 4,454,374 A | 6/1984 | Pollack |
| 4,501,269 A | 2/1985 | Bagby |
| 4,545,374 A | 10/1985 | Jacobson |
| 4,646,738 A | 3/1987 | Trott |
| 4,657,550 A | 4/1987 | Daher |
| 4,697,586 A | 10/1987 | Gazale |
| 4,743,256 A | 5/1988 | Brantigan |
| 4,781,591 A | 11/1988 | Allen |
| 4,834,757 A | 5/1989 | Brantigan |
| 4,877,020 A | 10/1989 | Vich |
| 4,878,915 A | 11/1989 | Brantigan |
| 4,932,975 A | 6/1990 | Main et al. |
| 4,950,296 A | 8/1990 | McIntyre |
| 4,961,740 A | 10/1990 | Ray et al. |
| 4,962,766 A | 10/1990 | Herzon |
| 5,015,247 A | 5/1991 | Michelson |
| 5,026,373 A | 6/1991 | Ray et al. |
| 5,047,055 A | 9/1991 | Bao et al. |
| 5,055,104 A | 10/1991 | Ray |
| 5,062,845 A | 11/1991 | Kuslich et al. |
| 5,071,437 A | 12/1991 | Steffee |
| 5,092,572 A | 3/1992 | Litwak et al. |
| 5,133,717 A | 7/1992 | Chopin |
| 5,133,755 A | 7/1992 | Brekke |
| 5,171,278 A | 12/1992 | Pisharodi |
| 5,192,327 A | 3/1993 | Brantigan |
| 5,217,497 A | 6/1993 | Mehdian |
| 5,263,953 A | 11/1993 | Bagby |
| 5,269,785 A | 12/1993 | Bonutti |
| 5,284,153 A | 2/1994 | Raymond et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,322,505 A | 6/1994 | Krause et al. |
| 5,334,205 A | 8/1994 | Cain |
| 5,336,223 A | 8/1994 | Rogers |
| 5,364,400 A | 11/1994 | Rego, Jr. et al. |
| 5,395,372 A | 3/1995 | Holt et al. |
| 5,397,363 A | 3/1995 | Gelbard |
| 5,397,364 A | 3/1995 | Kozak et al. |
| 5,401,269 A | 3/1995 | Büttner-Janz et al. |
| 5,405,391 A | 4/1995 | Henderson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,484,403 A | 1/1996 | Yoakum et al. |
| 5,484,437 A | 1/1996 | Michelson |
| 5,489,307 A | 2/1996 | Kuslich et al. |
| 5,489,308 A | 2/1996 | Kuslich et al. |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,688 A | 7/1996 | Navas |
| 5,545,222 A | 8/1996 | Bonutti |
| 5,545,688 A | 8/1996 | Huang |
| 5,562,736 A | 10/1996 | Ray et al. |
| 5,565,005 A | 10/1996 | Erickson et al. |
| 5,571,190 A | 11/1996 | Ulrich et al. |
| 5,571,192 A | 11/1996 | Schonhoffer |
| 5,593,409 A | 1/1997 | Michelson |
| 5,607,424 A | 3/1997 | Tropiano |
| 5,609,636 A | 3/1997 | Kohrs et al. |
| 5,611,800 A | 3/1997 | Davis et al. |
| 5,611,810 A | 3/1997 | Arnold et al. |
| 5,632,747 A | 5/1997 | Scarborough et al. |
| 5,645,596 A | 7/1997 | Kim et al. |
| 5,645,598 A | 7/1997 | Brosnahan, III |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,676,703 A | 10/1997 | Gelbard |
| 5,683,394 A | 11/1997 | Rinner |
| 5,683,400 A | 11/1997 | McGuire |
| 5,683,464 A | 11/1997 | Wagner et al. |
| 5,683,465 A | 11/1997 | Shinn et al. |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Margulies |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi |
| 5,707,373 A | 1/1998 | Sevrain et al. |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,722,977 A | 3/1998 | Wilhelmy |
| 5,728,159 A | 3/1998 | Stroever et al. |
| 5,741,253 A | 4/1998 | Michelson |
| 5,741,261 A | 4/1998 | Moskovitz et al. |
| 5,755,797 A | 5/1998 | Baumgartner |

(56) References Cited

U.S. PATENT DOCUMENTS

| | | |
|---|---|---|
| 5,766,252 A | 6/1998 | Henry et al. |
| 5,772,661 A | 6/1998 | Michelson |
| 5,775,331 A | 7/1998 | Raymond et al. |
| 5,775,797 A | 7/1998 | Henstra |
| 5,779,642 A | 7/1998 | Nightengale |
| 5,782,830 A | 7/1998 | Farris |
| 5,782,832 A | 7/1998 | Larsen et al. |
| 5,782,919 A | 7/1998 | Zdeblick et al. |
| 5,785,710 A | 7/1998 | Michelson |
| 5,797,909 A | 8/1998 | Michelson |
| 5,800,549 A | 9/1998 | Bao et al. |
| 5,800,550 A | 9/1998 | Sertich |
| 5,814,084 A | 9/1998 | Grivas et al. |
| 5,814,550 A | 9/1998 | Wolcott |
| 5,851,084 A | 12/1998 | Nishikawa |
| 5,851,208 A | 12/1998 | Trott |
| 5,860,973 A | 1/1999 | Michelson |
| 5,865,845 A | 2/1999 | Thalgott |
| 5,865,848 A | 2/1999 | Baker |
| 5,885,299 A | 3/1999 | Winslow et al. |
| 5,888,219 A | 3/1999 | Bonutti |
| 5,888,224 A | 3/1999 | Beckers et al. |
| 5,893,889 A | 4/1999 | Harrington |
| 5,893,890 A | 4/1999 | Pisharodi |
| 5,904,719 A | 5/1999 | Errico et al. |
| 5,910,315 A | 6/1999 | Stevenson et al. |
| 5,942,698 A | 8/1999 | Stevens |
| 5,954,769 A | 9/1999 | Rosenlicht |
| 5,968,098 A | 10/1999 | Winslow |
| 5,989,291 A | 11/1999 | Ralph et al. |
| 5,993,474 A | 11/1999 | Ouchi |
| 6,003,426 A | 12/1999 | Kobayashi et al. |
| 6,004,326 A | 12/1999 | Castro et al. |
| 6,008,433 A | 12/1999 | Stone |
| 6,015,436 A | 1/2000 | Schönhöffer |
| 6,033,405 A | 3/2000 | Winslow et al. |
| 6,033,438 A | 3/2000 | Bianchi et al. |
| 6,039,761 A | 3/2000 | Li et al. |
| 6,042,582 A | 3/2000 | Ray |
| 6,045,580 A | 4/2000 | Scarborough et al. |
| 6,045,582 A | 4/2000 | Prybyla |
| 6,048,342 A | 4/2000 | Zucherman et al. |
| 6,059,829 A | 5/2000 | Schlapfer et al. |
| 6,063,088 A | 5/2000 | Winslow |
| 6,063,121 A | 5/2000 | Xavier et al. |
| 6,080,155 A | 6/2000 | Michelson |
| 6,083,225 A | 7/2000 | Winslow et al. |
| 6,090,143 A | 7/2000 | Meriwether et al. |
| 6,096,080 A | 8/2000 | Nicholson et al. |
| 6,102,948 A | 8/2000 | Brosnahan, III |
| 6,120,503 A | 9/2000 | Michelson |
| 6,120,506 A | 9/2000 | Kohrs et al. |
| 6,132,472 A | 10/2000 | Bonutti |
| 6,143,033 A | 11/2000 | Paul et al. |
| 6,159,211 A | 12/2000 | Boriani et al. |
| 6,159,215 A | 12/2000 | Urbahns et al. |
| 6,193,756 B1 | 2/2001 | Studer et al. |
| 6,200,347 B1 | 3/2001 | Anderson et al. |
| 6,224,607 B1 | 5/2001 | Michelson |
| 6,224,631 B1 | 5/2001 | Kohrs |
| 6,241,769 B1 | 6/2001 | Nicholson et al. |
| 6,241,770 B1 | 6/2001 | Michelson |
| 6,241,771 B1 | 6/2001 | Gresser et al. |
| 6,245,108 B1 | 6/2001 | Biscup |
| 6,251,140 B1 | 6/2001 | Marino et al. |
| 6,258,125 B1 | 7/2001 | Paul et al. |
| 6,277,149 B1 | 8/2001 | Boyle et al. |
| 6,304,487 B1 | 10/2001 | Pawletko et al. |
| 6,309,421 B1 | 10/2001 | Pisharodi |
| 6,319,257 B1 | 11/2001 | Carignan et al. |
| 6,368,350 B1 | 4/2002 | Erickson et al. |
| 6,371,989 B1 | 4/2002 | Chauvin et al. |
| 6,383,221 B1 | 5/2002 | Scarborough et al. |
| 6,409,766 B1 | 6/2002 | Brett |
| 6,413,278 B1 | 7/2002 | Marchosky |
| 6,425,772 B1 | 7/2002 | Bernier et al. |
| 6,426,772 B1 | 7/2002 | Yoneyama et al. |
| 6,432,140 B1 | 8/2002 | Lin |
| 6,440,142 B1 | 8/2002 | Ralph et al. |
| 6,442,814 B1 | 9/2002 | Landry et al. |
| 6,447,546 B1 | 9/2002 | Bramlet et al. |
| 6,447,547 B1 | 9/2002 | Michelson |
| 6,454,806 B1 | 9/2002 | Cohen et al. |
| 6,468,311 B2 | 10/2002 | Boyd et al. |
| 6,491,724 B1 | 12/2002 | Ferree |
| 6,527,773 B1 | 3/2003 | Lin et al. |
| D472,634 S | 4/2003 | Anderson |
| D473,650 S | 4/2003 | Anderson |
| 6,547,823 B2 | 4/2003 | Scarborough et al. |
| 6,558,424 B2 | 5/2003 | Thalgott |
| 6,562,072 B1 | 5/2003 | Fuss et al. |
| 6,595,998 B2 | 7/2003 | Johnson et al. |
| 6,599,294 B2 | 7/2003 | Fuss et al. |
| 6,626,905 B1 | 9/2003 | Schmiel et al. |
| 6,635,086 B2 * | 10/2003 | Lin |
| 6,648,895 B2 | 11/2003 | Burkus et al. |
| 6,666,888 B1 | 12/2003 | Jackson |
| 6,666,889 B1 | 12/2003 | Commarmond |
| 6,672,019 B1 | 1/2004 | Wenz |
| 6,676,703 B2 | 1/2004 | Biscup |
| 6,706,067 B2 | 3/2004 | Shimp et al. |
| 6,723,097 B2 | 4/2004 | Fraser et al. |
| 6,743,255 B2 | 6/2004 | Ferree |
| 6,746,484 B1 | 6/2004 | Liu et al. |
| 6,755,841 B2 | 6/2004 | Fraser et al. |
| 6,761,739 B2 | 7/2004 | Shepard |
| 6,767,367 B1 | 7/2004 | Michelson |
| 6,802,863 B2 | 10/2004 | Lawson et al. |
| 6,824,564 B2 | 11/2004 | Crozet |
| 6,830,570 B1 | 12/2004 | Frey et al. |
| 6,835,208 B2 | 12/2004 | Marchosky |
| 6,843,804 B2 | 1/2005 | Bryan |
| D503,801 S | 4/2005 | Jackson |
| 6,923,814 B1 | 8/2005 | Hildebrand et al. |
| 6,942,697 B2 | 9/2005 | Lange et al. |
| 6,942,698 B1 | 9/2005 | Jackson |
| 6,964,687 B1 | 11/2005 | Bernard et al. |
| 6,974,480 B2 | 12/2005 | Messerli et al. |
| 6,979,353 B2 | 12/2005 | Bresina |
| 6,984,245 B2 | 1/2006 | McGahan et al. |
| 6,986,788 B2 | 1/2006 | Paul et al. |
| 6,989,031 B2 | 1/2006 | Michelson |
| 7,018,412 B2 | 3/2006 | Ferreira et al. |
| 7,018,416 B2 | 3/2006 | Hanson et al. |
| 7,056,344 B2 | 6/2006 | Huppert et al. |
| 7,060,073 B2 | 6/2006 | Frey et al. |
| 7,060,097 B2 * | 6/2006 | Fraser .................. A61F 2/442 623/17.13 |
| 7,060,099 B2 | 6/2006 | Carli et al. |
| 7,083,651 B2 | 8/2006 | Diaz et al. |
| D530,423 S | 10/2006 | Miles et al. |
| 7,115,144 B2 | 10/2006 | Diaz et al. |
| 7,125,425 B2 | 10/2006 | Foley et al. |
| 7,192,447 B2 | 3/2007 | Rhoda |
| 7,201,776 B2 | 4/2007 | Ferree et al. |
| 7,235,101 B2 * | 6/2007 | Berry .................. A61F 2/4455 623/17.14 |
| 7,244,258 B2 | 7/2007 | Burkus et al. |
| 7,303,583 B1 | 12/2007 | Schär et al. |
| 7,326,251 B2 | 2/2008 | McCombe et al. |
| 7,361,193 B2 | 4/2008 | Frey et al. |
| 7,442,211 B2 | 10/2008 | de Villiers et al. |
| 7,611,538 B2 | 11/2009 | Belliard et al. |
| 7,815,682 B1 | 10/2010 | Peterson et al. |
| 7,832,409 B2 | 11/2010 | Richelsoph et al. |
| 7,842,088 B2 | 11/2010 | Rashbaum et al. |
| 7,867,277 B1 | 1/2011 | Tohmeh |
| 7,918,891 B1 | 4/2011 | Curran et al. |
| 7,951,203 B2 | 5/2011 | McCombe et al. |
| 8,021,427 B2 | 9/2011 | Spoonamore |
| 8,021,430 B2 | 9/2011 | Michelson |
| 8,187,334 B2 | 5/2012 | Curran et al. |
| 8,246,686 B1 | 8/2012 | Curran et al. |
| 8,251,997 B2 | 8/2012 | Michelson |

(56) References Cited

U.S. PATENT DOCUMENTS

| | | |
|---|---|---|
| 8,287,572 B2 | 10/2012 | Bae |
| 8,361,156 B2 | 1/2013 | Curran et al. |
| 8,425,612 B2 | 4/2013 | Perez-Cruet et al. |
| 8,506,630 B2 | 8/2013 | Wardlaw |
| 8,506,636 B2 | 8/2013 | Dye |
| 8,574,301 B2 | 11/2013 | Curran et al. |
| 8,579,909 B2 | 11/2013 | Burkus et al. |
| 8,591,589 B2 | 11/2013 | McCombe et al. |
| 8,608,804 B2 | 12/2013 | Curran et al. |
| 8,900,307 B2 | 12/2014 | Hawkins et al. |
| 8,979,927 B2 * | 3/2015 | Huntsman ............. A61F 2/4455 623/17.11 |
| 9,907,672 B1 | 3/2018 | Raiszadeh |
| 10,779,816 B2 * | 9/2020 | Goldstein .......... A61B 17/8095 |
| 2001/0016741 A1 | 8/2001 | Burkus et al. |
| 2001/0016777 A1 | 8/2001 | Biscup |
| 2002/0019637 A1 | 2/2002 | Frey et al. |
| 2002/0035400 A1 | 3/2002 | Bryan et al. |
| 2002/0058950 A1 | 5/2002 | Winterbottom et al. |
| 2002/0068936 A1 | 6/2002 | Burkus et al. |
| 2002/0077702 A1 | 6/2002 | Castro |
| 2002/0111687 A1 | 8/2002 | Ralph et al. |
| 2002/0116008 A1 | 8/2002 | Lin et al. |
| 2002/0165550 A1 | 11/2002 | Frey et al. |
| 2002/0165613 A1 * | 11/2002 | Lin ........................ A61F 2/447 623/17.11 |
| 2003/0023306 A1 | 1/2003 | Liu et al. |
| 2003/0028249 A1 | 2/2003 | Baccelli et al. |
| 2003/0040802 A1 | 2/2003 | Errico et al. |
| 2003/0074076 A1 | 4/2003 | Ferree et al. |
| 2003/0100950 A1 | 5/2003 | Moret |
| 2003/0105527 A1 | 6/2003 | Bresina |
| 2003/0105528 A1 | 6/2003 | Shimp et al. |
| 2003/0109928 A1 | 6/2003 | Pasquet et al. |
| 2003/0139812 A1 | 7/2003 | Garcia et al. |
| 2003/0139813 A1 | 7/2003 | Messerli et al. |
| 2003/0149438 A1 | 8/2003 | Nichols et al. |
| 2003/0153975 A1 | 8/2003 | Byrd, III et al. |
| 2003/0167091 A1 | 9/2003 | Scharf |
| 2003/0208273 A1 | 11/2003 | Eisermann et al. |
| 2003/0220691 A1 | 11/2003 | Songer et al. |
| 2003/0233146 A1 | 12/2003 | Grinberg et al. |
| 2004/0002759 A1 | 1/2004 | Ferree |
| 2004/0024408 A1 | 2/2004 | Burkus et al. |
| 2004/0024460 A1 | 2/2004 | Ferree |
| 2004/0024461 A1 | 2/2004 | Ferree |
| 2004/0030398 A1 | 2/2004 | Ferree |
| 2004/0093087 A1 | 5/2004 | Ferree et al. |
| 2004/0117020 A1 | 6/2004 | Frey et al. |
| 2004/0117022 A1 | 6/2004 | Marnay et al. |
| 2004/0127990 A1 | 7/2004 | Bartish, Jr. et al. |
| 2004/0127991 A1 | 7/2004 | Ferree |
| 2004/0127994 A1 | 7/2004 | Kast et al. |
| 2004/0143332 A1 | 7/2004 | Krueger et al. |
| 2004/0148028 A1 | 7/2004 | Ferree et al. |
| 2004/0153155 A1 | 8/2004 | Chung et al. |
| 2004/0158254 A1 | 8/2004 | Eisermann |
| 2004/0158328 A1 | 8/2004 | Eisermann |
| 2004/0176775 A1 | 9/2004 | Burkus et al. |
| 2004/0186572 A1 | 9/2004 | Lange et al. |
| 2004/0193273 A1 | 9/2004 | Huang |
| 2004/0199251 A1 | 10/2004 | McCombe et al. |
| 2004/0215198 A1 | 10/2004 | Marnay et al. |
| 2004/0220567 A1 | 11/2004 | Eisermann et al. |
| 2004/0220668 A1 | 11/2004 | Eisermann et al. |
| 2004/0220670 A1 | 11/2004 | Eisermann et al. |
| 2004/0225365 A1 | 11/2004 | Eisermann et al. |
| 2004/0225366 A1 | 11/2004 | Eisermann et al. |
| 2004/0230307 A1 | 11/2004 | Eisermann |
| 2004/0243240 A1 | 12/2004 | Beaurain et al. |
| 2004/0260286 A1 | 12/2004 | Ferree |
| 2004/0267364 A1 | 12/2004 | Carli et al. |
| 2005/0021146 A1 | 1/2005 | de Villiers et al. |
| 2005/0038516 A1 | 2/2005 | Spoonamore |
| 2005/0043802 A1 | 2/2005 | Eisermann et al. |
| 2005/0043803 A1 | 2/2005 | Schultz et al. |
| 2005/0059971 A1 | 3/2005 | Michelson |
| 2005/0060034 A1 * | 3/2005 | Berry ........................ A61F 2/44 623/17.14 |
| 2005/0065611 A1 | 3/2005 | Huppert et al. |
| 2005/0125062 A1 | 6/2005 | Biedermann et al. |
| 2005/0149192 A1 * | 7/2005 | Zucherman ........ A61B 17/1671 623/17.11 |
| 2005/0149193 A1 | 7/2005 | Zucherman et al. |
| 2005/0187625 A1 | 8/2005 | Wolek et al. |
| 2005/0197702 A1 | 9/2005 | Coppes et al. |
| 2005/0203538 A1 | 9/2005 | Lo et al. |
| 2006/0041314 A1 | 2/2006 | Millard |
| 2006/0058876 A1 | 3/2006 | McKinley |
| 2006/0069440 A1 | 3/2006 | Zucherman et al. |
| 2006/0074488 A1 | 4/2006 | Abdou |
| 2006/0085071 A1 | 4/2006 | Lechmann et al. |
| 2006/0089714 A1 | 4/2006 | Liu et al. |
| 2006/0095132 A1 | 5/2006 | Kirschman |
| 2006/0111783 A1 | 5/2006 | Aflatoon et al. |
| 2006/0116768 A1 | 6/2006 | Krueger et al. |
| 2006/0142864 A1 | 6/2006 | Cauthen |
| 2006/0155377 A1 | 7/2006 | Beaurain et al. |
| 2006/0167549 A1 | 7/2006 | Mathys, Jr. et al. |
| 2006/0190084 A1 | 8/2006 | Doubler et al. |
| 2006/0235526 A1 | 10/2006 | Lemaire |
| 2006/0259144 A1 | 11/2006 | Trieu |
| 2007/0043442 A1 | 2/2007 | Abernathie et al. |
| 2007/0179612 A1 | 8/2007 | Johnson et al. |
| 2007/0191945 A1 | 8/2007 | Yu et al. |
| 2007/0233262 A1 | 10/2007 | Arnin et al. |
| 2007/0239278 A1 * | 10/2007 | Heinz ................... A61F 2/4425 623/17.15 |
| 2007/0260320 A1 | 11/2007 | Peterman et al. |
| 2007/0270951 A1 | 11/2007 | Davis et al. |
| 2007/0276495 A1 | 11/2007 | Aaron |
| 2007/0276499 A1 | 11/2007 | Paul et al. |
| 2007/0288007 A1 | 12/2007 | Burkus et al. |
| 2008/0009946 A1 | 1/2008 | Douget et al. |
| 2008/0015701 A1 | 1/2008 | Garcia et al. |
| 2008/0027550 A1 | 1/2008 | Link et al. |
| 2008/0058838 A1 | 3/2008 | Steinberg |
| 2008/0058940 A1 | 3/2008 | Wu et al. |
| 2008/0065219 A1 | 3/2008 | Dye |
| 2008/0082173 A1 | 4/2008 | Delurio et al. |
| 2008/0119937 A1 | 5/2008 | McCombe et al. |
| 2008/0183296 A1 | 7/2008 | Ferree |
| 2009/0036927 A1 | 2/2009 | Vestgaarden |
| 2009/0069895 A1 | 3/2009 | Gittings et al. |
| 2009/0076610 A1 | 3/2009 | Afzal |
| 2009/0143859 A1 | 6/2009 | McClellan, III et al. |
| 2009/0198339 A1 | 8/2009 | Kleiner et al. |
| 2009/0204219 A1 | 8/2009 | Beaurain et al. |
| 2009/0222099 A1 | 9/2009 | Liu et al. |
| 2010/0036497 A1 | 2/2010 | Lechmann et al. |
| 2010/0106250 A1 | 4/2010 | Abdou |
| 2010/0152853 A1 | 6/2010 | Kirschman |
| 2010/0211176 A1 | 8/2010 | Greenhalgh |
| 2010/0249936 A1 | 9/2010 | Bertagnoli |
| 2010/0262246 A1 | 10/2010 | Attia |
| 2011/0054617 A1 | 3/2011 | Sekhon et al. |
| 2011/0082552 A1 | 4/2011 | Wistrom et al. |
| 2011/0112642 A1 | 5/2011 | Tohmeh |
| 2011/0160866 A1 * | 6/2011 | Laurence ............... A61F 2/4465 623/17.16 |
| 2011/0196496 A1 | 8/2011 | McCombe et al. |
| 2012/0078374 A1 | 3/2012 | Villiers et al. |
| 2012/0158141 A1 | 6/2012 | Johnson et al. |
| 2012/0179261 A1 | 7/2012 | Soo |
| 2012/0191190 A1 | 7/2012 | Trieu |
| 2012/0209388 A1 | 8/2012 | Curran et al. |
| 2012/0215317 A1 | 8/2012 | Curran et al. |
| 2013/0006363 A1 | 1/2013 | Ullrich, Jr. et al. |
| 2013/0138216 A1 | 5/2013 | Curran et al. |

(56) References Cited

U.S. PATENT DOCUMENTS

| | | |
|---|---|---|
| 2013/0144390 A1 | 6/2013 | Curran et al. |
| 2013/0245771 A1 | 9/2013 | Michelson |

FOREIGN PATENT DOCUMENTS

| | | | |
|---|---|---|---|
| EP | 0667127 | A1 | 8/1995 |
| EP | 0706876 | A1 | 4/1996 |
| EP | 0716840 | A2 | 6/1996 |
| EP | 0517030 | B1 | 9/1996 |
| EP | 0737448 | A1 | 10/1996 |
| EP | 0796593 | A2 | 9/1997 |
| EP | 0809974 | A3 | 4/1998 |
| EP | 0809975 | A3 | 4/1998 |
| EP | 0811356 | A3 | 4/1998 |
| EP | 0880938 | A1 | 12/1998 |
| WO | 1990000037 | A1 | 1/1990 |
| WO | 1991006261 | A1 | 5/1991 |
| WO | 1992014423 | A1 | 9/1992 |
| WO | 1993001771 | A1 | 2/1993 |
| WO | 1994004100 | A1 | 3/1994 |
| WO | 1994010928 | A1 | 5/1994 |
| WO | 1995001810 | A1 | 1/1995 |
| WO | 1995008306 | A1 | 3/1995 |
| WO | 1996008205 | A1 | 3/1996 |
| WO | 1996017564 | A1 | 6/1996 |
| WO | 1996041582 | A1 | 12/1996 |
| WO | 1997020513 | A1 | 6/1997 |
| WO | 1997033525 | A1 | 9/1997 |
| WO | 1997037620 | A1 | 10/1997 |
| WO | 1998009586 | A1 | 3/1998 |
| WO | 1998014142 | A1 | 4/1998 |
| WO | 1998017208 | A2 | 4/1998 |
| WO | 1998025539 | A1 | 6/1998 |
| WO | 1999008627 | A1 | 2/1999 |
| WO | 1999038461 | A2 | 8/1999 |
| WO | 2000044288 | A1 | 8/2000 |
| WO | 2000045712 | A1 | 8/2000 |
| WO | 2000045713 | A1 | 8/2000 |
| WO | 2001041681 | A1 | 6/2001 |
| WO | 2001049333 | A2 | 7/2001 |
| WO | 2004098380 | A2 | 11/2004 |
| WO | 2005058141 | A2 | 6/2005 |
| WO | 2007003437 | A2 | 1/2007 |

OTHER PUBLICATIONS

Baulot et al., "Complementary anterior spondylodesis by thoracoscopy. Technical note regarding an observation", Lyon Surg., 1994, pp. 347-351, 90, No. 5.

Benini et al., "Undercutting decompression and posterior fusion with translaminar facet screw fixation in degenerative lumbar spinal stenosis: Technique and results", Neuro-Orthopedics, 1995, pp. 159-172, 17/18.

Berry et al., "A morphometric study of human lumbar and selected thoracic vertebrae", Spine, 1987, pp. 362-367, 12, No. 4.

CoRoent® XL & XLR Marketing Brochure (9004225 B.0), NuVasive, Inc., 2006, 2 pgs.

CoRoent® XL & XLR Marketing Brochure (9004225 C.0), NuVasive, Inc., 2007, 2 pgs.

CoRoent® XL Marketing Brochure (9500039 A.0), NuVasive, Inc., 2006, 8 pgs.

CoRoent™ Marketing Brochure (9004001 A.0), NuVasive, Inc., 2004, 2 pgs.

CoRoent™ Marketing Brochure (9004001 C.0), NuVasive, Inc., 2005, 2 pgs.

CoRoent™ XL & XLR Marketing Brochure (9004225 A.0), NuVasive, Inc., 2005, 2 pgs.

Counterclaim Defendants' Corrected Amended Invalidity Contentions re U.S. Pat. Nos. 8,000,782; 8,005,535; 8,016,767; 8,192,356; 8,187,334; 8,361,156, D. 652,922; D. 666,294 re Case No. 3:12-cv-02738-CAB(MDD), dated Aug. 19, 2013, 30 pgs.

Crock, "A short practice of spinal surgery", 1993, Springer-Verlag/Wein, New York, 251 pgs.

Crock, "Anterior lumbar interbody fusion", Clinical Orthopaedics and Related Research, 1982, pp. 157-163, 165.

Decision denying Institution of Inter Partes Review in IPR2013-00504, dated Feb. 13, 2014, 9 pgs.

Decision denying Institution of Inter Partes Review in IPR2013-00506, dated Feb. 13, 2014, 21 pgs.

Decision denying Institution of Inter Partes Review in IPR2013-00507, dated Feb. 13, 2014, 15 pgs.

Decision denying Institution of Inter Partes Review in IPR2013-00508, dated Feb. 13, 2014, 14 pgs.

Declaration of Dr. Hansen A. Yuan from IPR2013-00506, dated May 21, 2014, 63 pgs.

Declaration of Dr. Hansen A. Yuan from IPR2013-00507, dated May 21, 2014, 85 pgs.

Declaration of Dr. Hansen A. Yuan from IPR2013-00508, dated May 21, 2014, 85 pgs.

Declaration of Mary Phelps regarding Telamon Verte-Stack PEEK Vertebral Body Spacer, dated Aug. 13, 2013, 9 pgs.

Declaration of Richard A. Hynes, M.D. regarding U.S. Pat. No. 8,187,334, dated Aug. 14, 2013, 74 pgs.

Declaration of Richard A. Hynes, M.D. regarding U.S. Pat. No. 8,361,156, dated Aug. 14, 2013, 74 pgs.

Declaration of Steven D. DeRidder regarding U.S. Patent Application Publication No. 2002/0165550, dated Jul. 30, 2013, 5 pgs.

Edeland, "Some additional suggestions for an intervertebral disc prosthesis", Journal of Biomedical Engineering, 1985, pp. 57-62, 7.

Final Written Decision in *Medtronic, Inc. v. NuVasive, Inc.*, Case IPR2013-00507, dated Feb. 11, 2015, 14 pgs.

Final Written Decision in *Medtronic, Inc. v. NuVasive, Inc.*, Case IPR2013-00508, dated Feb. 11, 2015, 19 pgs.

Kambin et al., "History and current status of percutaneous arthroscopic disc surgery", Spine, 1996, pp. 57S-61S, 21, No. 24S.

Kemp et al., "Anterior fusion of the spine for infective lesions in adults", The Journal of Bone and Joint Surgery, 1973, pp. 715-734, 55 B, No. 4.

Medtronic Sofamor Danek Boomerang brochure, Medtronic Sofamor Danek, 2003, 6 pages.

Medtronic Sofamor Danek USA, Inc. "Boomerang I Verte-Stack PEEK Vertebral Body Brochure," 2003, 6 pages.

Medtronic Sofamor Danek USA, Inc. "Boomerang I Verte-Stack PEEK Vertebral Body Spacer Implant," Apr. 26, 2001, 8 pages.

Medtronic Sofamor Danek USA, Inc. "Boomerang II Verte-Stack PEEK Vertebral Body Spacer Brochure," 2004, 4 pages.

Medtronic Sofamor Danek USA, Inc. "Boomerang II Verte-Stack PEEK Vertebral Body Spacer Implant," Dec. 17, 2003, 9 pages.

Medtronic Sofamor Danek USA, Inc. "Boomerang Prototype Verte-Stack PEEK Vertebral Body Spacer Implant," May 7, 2000, 8 pages.

Medtronic Sofamor Danek USA, Inc. "PCR PEEK Cement Restrictor Brochure," 2001, 2 pages.

Medtronic Sofamor Danek USA, Inc. "PCR PEEK Cement Restrictor Implant," Oct. 2, 2001, 17 pages.

Medtronic Sofamor Danek USA, Inc. "Telamon Verte-Stack PEEK Vertebral Body Spacer Brochure I," 2003, 2 pages.

Medtronic Sofamor Danek USA, Inc. "Telamon Verte-Stack PEEK Vertebral Body Spacer Brochure II," 2003, 10 pages.

Medtronic Sofamor Danek USA, Inc. "Telamon Verte-Stack PEEK Vertebral Body Spacer Implant," Oct. 2, 2001, 6 pages.

NuVasive Inc's Patent Owner Response in IPR2013-00506, dated May 21, 2014, 66 pgs.

NuVasive Inc's Patent Owner Response in IPR2013-00507, dated May 21, 2014, 50 pgs.

NuVasive Inc's Patent Owner Response in IPR2013-00508, dated May 21, 2014, 66 pgs.

Nuvasive, Inc., Corrected Final Invalidity Contentions Regarding U.S. Pat. No. 5,860,973, U.S. Pat. No. 6,592,586 and U.S. Pat. No. 6,945,933 filed in the United States District Court, Southern District of California on Jun. 14, 2010 (and 23 appendices).

Patent Owner NuVasive Inc.'s Preliminary Response in IPR2013-00504, dated Nov. 25, 2013, 40 pgs.

Patent Owner NuVasive Inc.'s Preliminary Response in IPR2013-00506, dated Nov. 25, 2013, 38 pgs.

(56) References Cited

OTHER PUBLICATIONS

Patent Owner NuVasive Inc.'s Preliminary Response in IPR2013-00507, dated Nov. 25, 2013, 29 pgs.
Patent Owner NuVasive Inc.'s Preliminary Response in IPR2013-00508, dated Nov. 25, 2013, 38 pgs.
Petition for Inter Partes Review of U.S. Pat. No. 8,187,334 Pursuant to 35 U.S.C. 311-319, 37 C.F.R. 42, dated Aug. 14, 2013, 64 pgs.
Petition for Inter Partes Review of U.S. Pat. No. 8,361,156 Pursuant to 35 U.S.C. 311-319, 37 C.F.R. 42, dated Aug. 14, 2013, 64 pgs.

* cited by examiner

IMPLANTS AND METHODS FOR SPINAL FUSION

CROSS-REFERENCES TO RELATED APPLICATIONS

This application is a continuation of U.S. patent application Ser. No. 15/906,534 filed Feb. 27, 2018, which is a continuation of U.S. patent application Ser. No. 14/924,490 filed Oct. 27, 2015, which is a continuation of U.S. patent application Ser. No. 13/337,967 filed Nov. 27, 2011, which is a continuation of U.S. patent application Ser. No. 12/380,693 filed Mar. 2, 2009, which claims the benefit of priority to U.S. Provisional Patent Application No. 61/067,700 filed Feb. 29, 2008, and U.S. Provisional Patent Application No. 61/105,796 filed Oct. 15, 2008, the entire contents of which are each incorporated by reference as if set forth herein in their entireties.

FIELD

This application relates generally to spinal fusion implants and methods for fusing spinal vertebrae.

BACKGROUND

Currently there are nearly 750,000 spine lumbar and cervical fusion procedures performed each year in the United States. These procedures are commonly performed to correct problems with displaced, damaged, or degenerated intervertebral discs due to trauma, disease, or aging. One of the most common of these procedures is spinal fusion, which involves removing some or the all of the diseased or damaged disc, inserting one or more intervertebral spacers to restore the natural height of the disc space, and allowing a bony bridge to form through the disc space fusing the adjacent vertebrae together. Increasingly, so-called "total disc replacement" (TDR) procedures are being utilized as an alternative to spinal fusion. Total disc replacements represent a new wave of spinal technology and generally involve implantation of mechanical devices designed to replace the functions of the intervertebral disc and thus preserve motion that is lost through a spinal fusion. While several different approaches may be used to access the target spine (the most common being anterior, posterior, and posterolateral approaches), the anterior approach is often utilized, especially for TDR, because it allows for greater exposure and a more complete excision of the damaged disc than the other common approaches.

Sometimes after a spinal fusion or TDR procedure it becomes necessary to remove and/or replace the previously implanted implant. During such revision surgeries it may be preferable, though not necessary, to access the spinal target site from a different approach than that used in the original surgery. This presents a challenge, however, when performing a revision of an anterior procedure because the implants deposited during an anterior procedure are generally too large to be removed through the smaller access corridors achievable with the other traditional spinal approaches (e.g. posterior and postero-lateral). As an alternative, recent advances in both technology and methodology have made the lateral approach to the spine a viable surgical option. The lateral approach has proven to be a safe and effective means for performing spinal fusion and, unlike the posterior and postero-lateral approaches, the lateral approach allows for access to the disc space which is comparable to that gained through the anterior approach.

One difficulty with utilizing a lateral approach for revision surgery is the absence of the Anterior Longitudinal Ligament (ALL) which is removed during the original procedure for the anterior approach to the spine. With the ALL barrier removed, the lateral implant may be more susceptible to expulsion. A need therefore exists for interbody implants configured for insertion through a lateral approach to the spine and resistant to anterior expulsion.

SUMMARY

Example embodiments of a fusion implant are described herein in accordance with aspects of the present invention. After insertion into a prepared disc space between adjacent vertebral bodies the fusion implant maintains a desired spatial arrangement between the adjacent vertebrae and facilitates the formation of a bony bridge between them. The embodiments shown herein are designed preferably for implantation into the disc space through a lateral approach. The implant may be comprised of any suitable bio-compatible material or a combination of multiple bio-compatible materials. Preferably, at least a portion of the spinal fusion implant may comprise a non-bone composition having radiolucent characteristics, including but not limited to polymer compositions (e.g. poly-ether-ether-ketone (PEEK) and/or poly-ether-ketone-ketone (PEKK)) or any combination of PEEK and PEKK. Other suitable materials used in the construction of implant may include but are not limited to ceramics and metals, such as titanium, by way of example only.

The fusion implants may be provided in any number of sizes by varying one or more of the implant height, width, and length. The dimensions of the implant may be altered according to proportions of the particular patient and/or further variation of the implant dimensions may be implemented to produce implants generally appropriate for implantation into either of the thoracic spine and the cervical spine.

Fusion may be facilitated or augmented by introducing or positioning various osteoinductive materials within the fusion implant and/or adjacent to the spinal fusion implant. Such osteoinductive materials may be introduced before, during, or after the insertion of the implant, and may include (but are not necessarily limited to) autologous bone harvested from the patient, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers.

The implant generally comprises an implant body and a keel structure. The implant body has a leading side and a trailing side at opposing ends along a longitudinal axis. Between the leading side and trailing side are an upper surface, a lower surface, an anterior side, and a posterior side. To maintain the disc space according to the natural curvature of the spine, the anterior side of the implant may possess a greater height dimension than the posterior side, such that upper surface and lower surface converge toward one another at posterior side. An implant with this configuration (i.e. a taller anterior side) is tailored to accommodate the natural lordotic curvature found in the lumbar and cervical spine. Alternatively, the implant may have a posterior side possessing a greater height dimension than an anterior side so as to accommodate the natural kyphotic curvature of the thoracic spine. In another alternative, the implant may have anterior and posterior sides of approximately the same height. Each of the upper surface and lower surface may be one of, or a combination of, generally planar, concave, and convex.

The body of the implant may be configured with at least one large fusion aperture and preferably includes between two and four large fusion apertures. The fusion apertures may be separated by a medial and/or longitudinal support, extending in a vertical fashion between upper surface and lower surface. The fusion apertures function primarily as an avenue for bony fusion between adjacent vertebrae. The spinal fusion implant may also have a plurality of visualization apertures extending through the anterior side and posterior side, which allow a user to assess the degree of bony fusion through visual observations (via X-ray, fluoroscopy, or other imaging technology), un-obscured by anterior side or posterior side.

The fusion implant may include anti-migration features designed to increase the traction between the spinal fusion implant and the contact surface of the adjacent vertebral bodies to guard against movement or slippage of the implant after implantation. Anti-migration features may include angled ridges provided along the upper surface and/or lower surface. Other anti-migration features may include one or more spike members disposed at various locations along the implant. The implant may include a total of six spike members disposed along each of the upper surface and the lower surface. The spike members may be manufactured from any of a variety of suitable materials, including but not limited to a metal, ceramic, and/or polymer material. Spike members may be provided having radiopaque characteristics. When the spike members are provided having radiodense characteristics and at least a portion of the implant is manufactured from a radiolucent material (such as, by way of example only, PEEK and/or PEKK), the spike members will be readily observable under X-ray or fluoroscopy such that a surgeon may track the progress of the implant during implantation and/or the placement of the implant after implantation. The spike members of the implant may include a male element and a female element which threadably engage each other through the implant body and clamp keel structures to the implant body. Alternatively, the spike members may each comprise a unitary element extending through the upper surface and lower surface. The spike elements may include a threaded end that engages the holes through the implant body and/or keel structures to hold keel structures to the body. The spike members may comprise a shorter element which only extends through a single surface. Additionally, while referred to as spike elements and shown with pointed tips, the spike elements may include other shapes configured to engage the vertebral endplates.

Additional members in the form of keel structures augment the anti-migration features of the implant and further stabilize the position of the implant within the disc space. Keel structures may extend above the upper surface and/or below the lower surface along at least a portion of the longitudinal axis of implant between leading side and trailing side. Keel structures may be canted or generally perpendicular to the surface from which they extend. The keel structures may extend along the approximate centerline of the implant. Alternatively, the keels may be situated nearer to one of the anterior side and posterior side. During implantation the keel structures are inserted into keel channels formed in the adjacent vertebrae. Apertures may be provided along the length of the keel, or a portion thereof, to permit bony ingrowth through the keel structures.

The keel structures can be made from the same material as the implant body or they can be made from a different material, or combination of materials. By way of example, the keel structures may be comprised of a metal (e.g. titanium) and the implant body may be comprised of a polymer (e.g. PEEK or PEKK). Alternatively, the keel may be comprised of a polymer (e.g. PEEK or PEKK) and the implant may also be comprised of a polymer (e.g. PEEK or PEKK). Similarly, the implant body and keel structures may be formed as a single part, or as a combination of parts.

The leading side of the implant may be tapered to facilitate insertion of the implant into the disc space between adjacent vertebrae. The trailing side of the implant may possess mating structures configured for engagement with an insertion instrument. The mating structures may include a threaded receiving aperture and a pair of grooved purchase regions extending generally horizontally from either side of the receiving aperture. The receiving aperture may extend inwardly from the trailing side in a generally perpendicular fashion relative to the trailing side and may be dimensioned to threadably receive a threaded connector on the insertion instrument. The grooved purchase regions are dimensioned to receive corresponding distal head ridges on the insertion instrument, which collectively provide an enhanced engagement between the implant and insertion instrument.

According to one example, a trial sizer and keel cutter instrument may be provided. The trial sizer may be inserted into the interbody disc space to determine the appropriate size implant required to achieved the desired disc height. The keel cutter may be guided along grooves in the trial sizer and advanced into the interbody disc space to form channels in the vertebral bodies for receiving the keel structures. The inserter may releasably attaches at its distal end to an implant for advancement and depositing of the implant within the interbody disc space after the channels have been formed. A threadable attachment means is shown, but other means of releasable attachment are contemplated.

BRIEF DESCRIPTION OF THE DRAWINGS

Many advantages of the present invention will be apparent to those skilled in the art with a reading of this specification in conjunction with the attached drawings, wherein like reference numerals are applied to like members and wherein.

DETAILED DESCRIPTION

Figure 1:
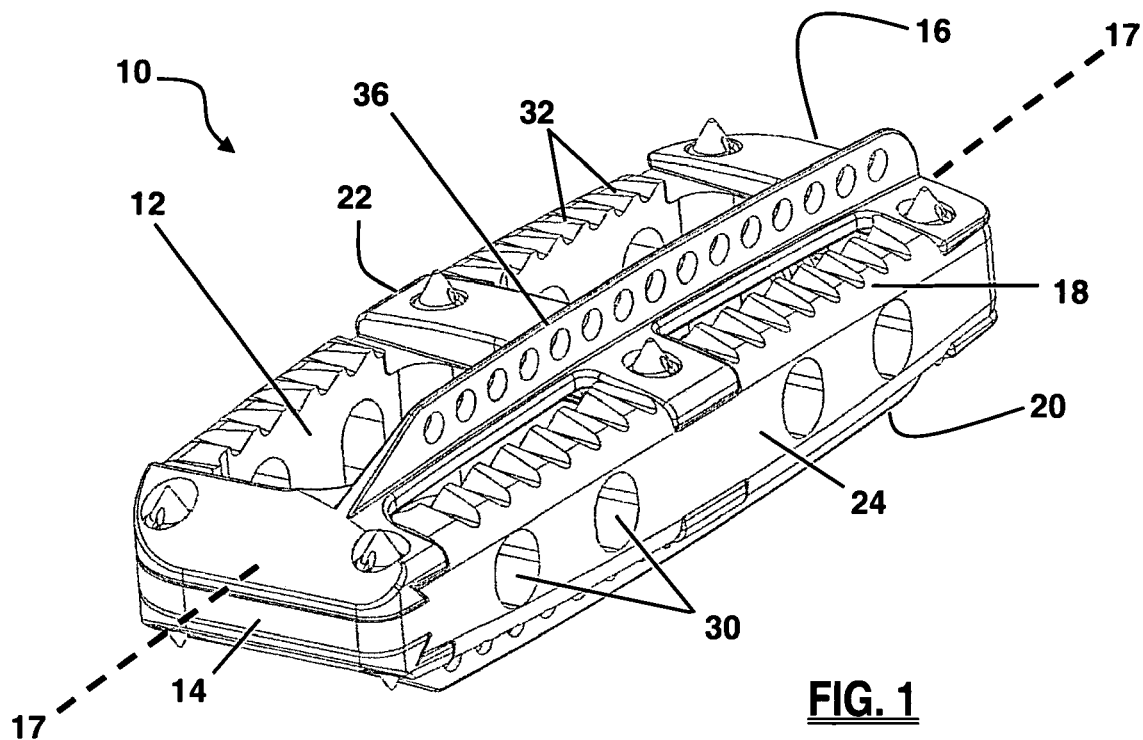
FIG. 1 is a perspective view of a spinal fusion implant including a keel structure, according to one embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with implant-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The implants disclosed herein boasts a variety of inventive features and components that warrant patent protection, both individually and in combination.

Example embodiments of a fusion implant are described herein in accordance with aspects of the present invention. After insertion into a prepared disc space between adjacent vertebral bodies the fusion implant maintains a desired spatial arrangement between the adjacent vertebrae and facilitates the formation of a bony bridge between them. The embodiments shown herein are designed for implantation into the disc space through a lateral (e.g. trans-psoas) access corridor. The implant may be comprised of any suitable bio-compatible material or a combination of multiple bio-compatible materials. Preferably, at least a portion of the spinal fusion implant may comprise a non-bone composition having radiolucent characteristics, including but not limited to polymer compositions (e.g. poly-ether-ether-ketone (PEEK) and/or poly-ether-ketone-ketone (PEKK)) or any combination of PEEK and PEKK. Other suitable materials used in the construction of the implants may include but are not limited to ceramics and metals, such as titanium, by way of example only.

The fusion implants may be provided in any number of sizes by varying one or more of the implant height, width, and length. By way of example only, the implant may be provided with a length dimension ranging from 30 mm to 60 mm. By way of further example, the implant may be provided with a width dimension ranging from 15 mm to 22 mm. By way of still further example, the implant may be provided with a height dimension ranging from 5 mm to 22 mm. The size ranges described are those generally appropriate for implantation into the lumbar spine. The dimensions of the implant may be altered according to proportions of the particular patient and/or further variation of the implant dimensions may be implemented to produce implants generally appropriate for implantation into either of the thoracic spine and the cervical spine.

Fusion may be facilitated or augmented by introducing or positioning various osteoinductive materials within the fusion implant and/or adjacent to the spinal fusion implant. Such osteoinductive materials may be introduced before, during, or after the insertion of the implant, and may include (but are not necessarily limited to) autologous bone harvested from the patient, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers.

Figure 2:
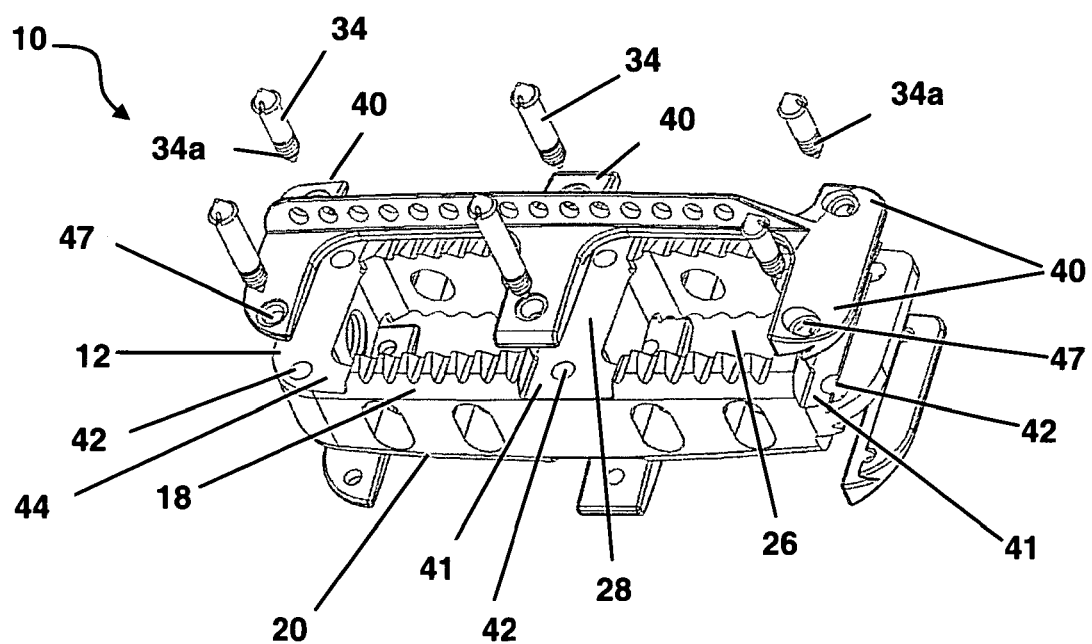
FIG. 2 is an exploded perspective view of the fusion implant of FIG. 1.
Figure 3:
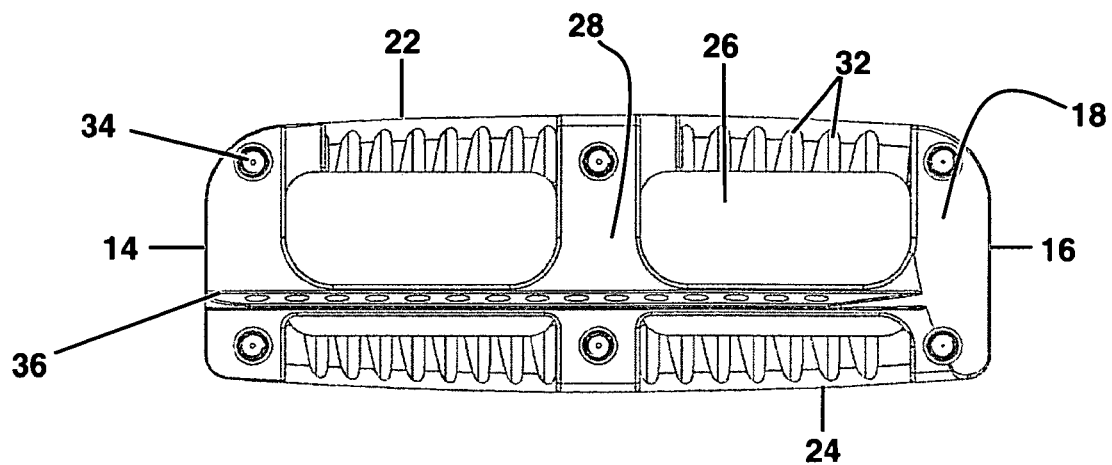
FIG. 3 is a top view of the fusion implant of FIG. 1.
Figure 4:
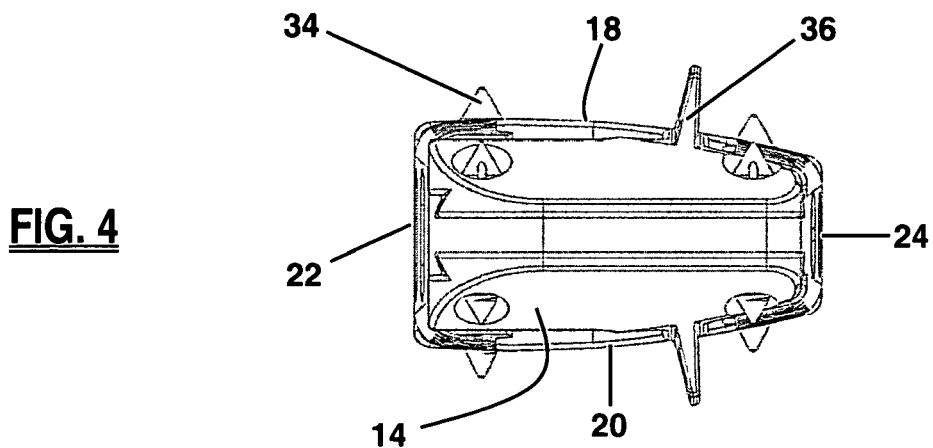
FIG. 4 a frontal view of the leading side of the implant of FIG. 1.
Figure 5:
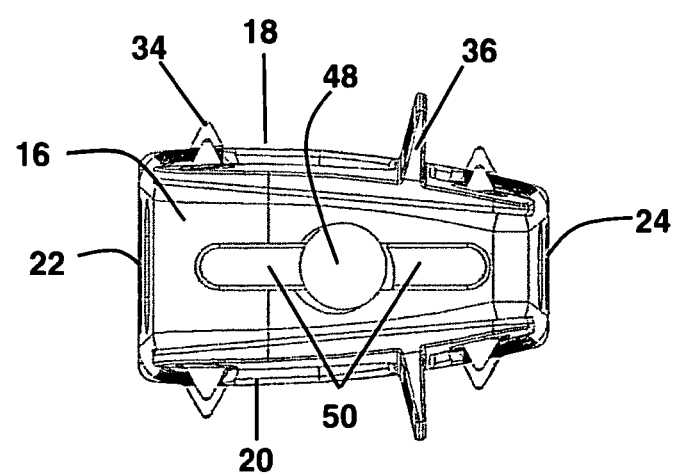
FIG. 5 a back view of the trailing side of the implant of FIG. 1.

FIGS. 1-8 depict an example of a spinal fusion implant 10 according to a first example embodiment. The implant 10 generally comprises an implant body 12 and a keel structure 36. The implant body 12 has a leading side 14 and a trailing side 16 at opposing ends along a longitudinal axis 17. As best illustrated in FIGS. 4-5, between the leading side 14 and trailing side 16 are an upper surface 18, a lower surface 20, an anterior side 22, and a posterior side 24. To maintain the disc space according of the natural curvature of the spine, the anterior side 22 of the implant may possess a greater height dimension than the posterior side 24, such that upper surface 18 and lower surface 20 converge toward one another at posterior side 24. By way of example only, the heights of anterior side 22 and posterior side 24 may be configured to provide a degree of curvature within a range of 1.degree.-20.degree. An implant with this configuration (i.e. a taller anterior side) is tailored to accommodate the natural lordotic curvature found in the lumbar and cervical spine. In another embodiment (not shown), an implant may have a posterior side 24 possessing a greater height dimension than an anterior side 22 so as to accommodate the natural kyphotic curvature of the thoracic spine. Each of the upper surface 18 and lower surface 20 may be one of, or a combination of, generally planar, concave, and convex.

As illustrated in FIG. 2, the body 12 of the implant 10 may be configured with at least one large fusion aperture 26. As shown, implant 10 has two large fusion apertures 26, separated by a medial support 28, extending in a vertical fashion between upper surface 18 and lower surface 20. The fusion apertures 26 function primarily as an avenue for bony fusion between adjacent vertebrae. Fusion apertures 26 may be provided in any of a variety of suitable shapes, including but not limited to the generally rectangular shape best viewed in FIG. 3, or a generally circular, oblong, polygonal, and/or triangular shape, or any combination thereof. As seen in FIG. 1, the spinal fusion implant 10 may also have a plurality of visualization apertures 30 situated between the anterior side 22 and posterior side 24, which allow a user to assess the degree of bony fusion through visual observations (via X-ray, fluoroscopy, or other imaging technology), unobscured by anterior side 22 or posterior side 24. The visualization apertures 30 may be provided in any of a variety of suitable shapes, including but not limited to the generally oblong shape best viewed in FIG. 1, or a generally circular, rectangular and/or triangular shape, or any combination thereof.

As best illustrated in FIGS. 1 and 3, the fusion implant 10 may include anti-migration features designed to increase the traction between the spinal fusion implant 10 and the contact surface of the adjacent vertebral bodies to guard against movement or slippage of the implant 10 after implantation. Anti-migration features may include angled ridges 32 provided along the upper surface 18 and/or lower surface 20. The angled ridges 32 may be oriented such that they do not resist movement in the direction of insertion (i.e. the leading side 14 entering the intradiscal space first) but do resist movement in the opposing direction. This allows the implant 10 to be inserted without the need for excessive force that may cause damage to the vertebrae and/or the implant, while still preventing the implant from moving in a direction where natural barriers (e.g. the annulus fibrosis or surrounding ligaments) have been removed for access to the disc space for implant insertion.

Other anti-migration features may include one or more spike members 34 disposed at various locations along the implant 10, as best illustrated in FIGS. 2-3. The implant 10 may include a total of six spike members 34 disposed along each of the upper surface 18 and the lower surface 20. The spike members 34 may be manufactured from any of a variety of suitable materials, including but not limited to a metal, ceramic, and/or polymer material. Spike members 34 may be provided having radiopaque characteristics. When the spike members 34 are provided having radiodense characteristics and at least a portion of the implant 10 is manufactured from a radiolucent material (such as, by way of example only, PEEK and/or PEKK), the spike members 34 will be readily observable under X-ray or fluoroscopy such that a surgeon may track the progress of the implant 10 during implantation and/or the placement of the implant 10 after implantation.

Additional members in the form of keel structures 36 augment the anti-migration features of implant 10 and further stabilize the position of the implant 10 within the disc space. Keel structures 36 may extend above the upper surface 18 and/or below the lower surface 20 along at least a portion of the longitudinal axis 17 of implant 10 between leading side 14 and trailing side 16. By way of example only, keel structures may rise approximately 2.5 mm from the upper and/or lower surfaces 18, 20. As best pictured in FIGS. 4-5, keel structures 36 may be canted and offset from the centerline of implant 10 such that the keel is positioned nearer to one of the anterior side 22 or posterior side 24 (as pictured). During implantation the keel structures 36 are inserted into keel channels formed in the adjacent vertebrae. Apertures 38 provided along the length of the keel, or a portion thereof, permit bony ingrowth through the keel structures. This serves to further integrate the implant 10 into the vertebrae. Alternatively (or in addition), the keel structures may be roughened and/or coated with bone growth promoting materials to further enhance the fusion process.

Figure 8:
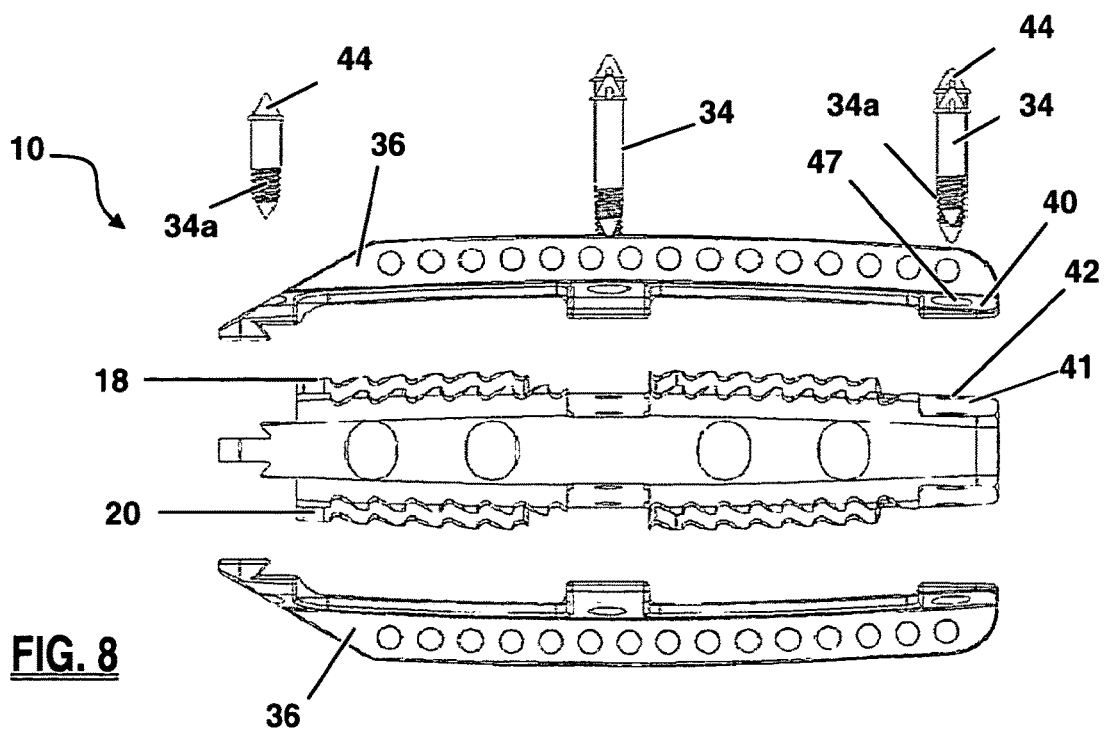
FIG. 8 an exploded side view of the posterior side of the implant of FIG. 1.

The keel structures 36 can be made from the same material as implant body 12 or they can be made from a different material, or combination of materials. In this first embodiment, by way of example, the keel structures 36 are comprised of a metal (e.g. titanium) and the implant body is comprised of a polymer (e.g. PEEK or PEKK). It will be appreciated, however, that both the implant body 12 and keel structures 36 could be made from a polymer material or, both could be made of a metal material. Similarly, the implant body 12 and keel structures 36 may be formed as a single part, or as a combination of parts. By way of example, as illustrated in FIGS. 2 and 8, the implant 10 is formed by two keel structures 36 mated to the implant body 12 via spike members 34. The keel structure 36 includes a sextet of mating arms 40 configured to rest on mating shelves 41 of body 12. Spike bores 47 situated on the mating arms 40 are aligned with corresponding holes 42 formed through implant body 12. Spike members 34 are placed through the holes 47 and 42 along the upper surface. Bores 47 in the lower keel structure (and optionally the upper keel structure and holes 42 of implant 10) may be threaded. The spike members 34 include a threaded region 34a, that is threadedly advanced through the bores 47. Ridges 44 on spike member 34 engage the keel structure around spike bores 47 prevent the spike member 34 from passing all the way through the upper keel structure and thus drawing and holding the keel structures and implant together as the spike 34 is threadedly engaged thereto.

Figure 6:
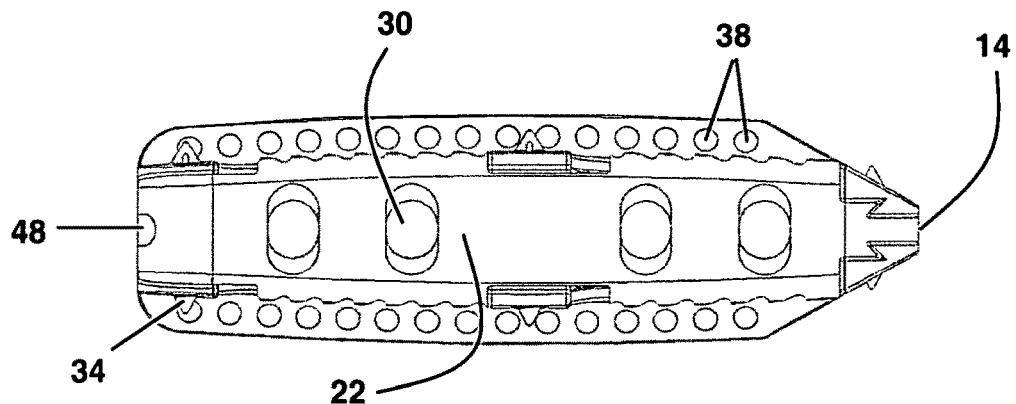
FIG. 6 is a side view of the anterior side of the implant of FIG. 1.
Figure 7:
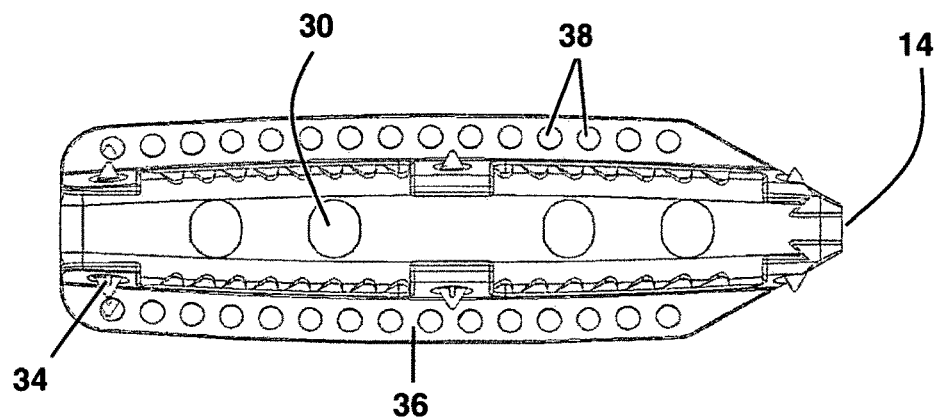
FIG. 7 is a side view of the posterior side of the implant of FIG. 1.
Figure 49:
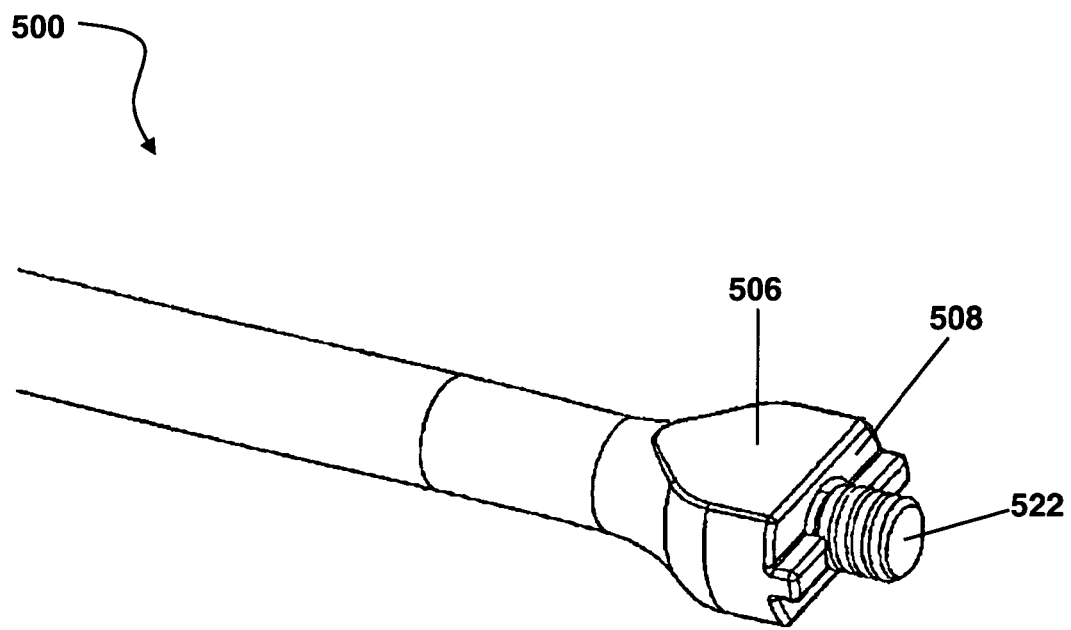
FIG. 49 is frontal perspective view of the insertion instrument of FIG. 48.

As illustrated in FIGS. 6-7, the leading side 14 of implant 10 may be tapered to facilitate insertion of the implant 10 into the disc space between adjacent vertebrae. With reference to FIG. 5, the trailing side 16 of implant 10 may possess mating structures configured for engagement with an insertion instrument (described below). According to the embodiment shown, the mating structures include a threaded receiving aperture 48 and a pair of grooved purchase regions 50 extending generally horizontally from either side of the receiving aperture 48. The receiving aperture 48 extends inwardly from the trailing side 16 in a generally perpendicular fashion relative to the trailing side 16 and is dimensioned to threadably receive a threaded connector 522 on the insertion instrument 500, as shown in FIG. 49, described below. The grooved purchase regions 50 are dimensioned to receive corresponding distal head ridges 508 on the insertion instrument 500, which collectively provide an enhanced engagement between the implant 10 and insertion instrument 500. After keel channels have been formed in the vertebrae neighboring the affected disc space, the implant 10 is releasably attached to the insertion instrument 500, the keels 36 are aligned with the keel channels, and the implant inserted into position. Thereafter the insertion instrument is detached from the implant 10 and removed from the patient.

FIGS. 9-16 depict an example of a spinal fusion implant 110 according to a second embodiment of the present invention. The implant 110 generally comprises an implant body 112 and a keel structure 136. The implant body 112 has a leading side 114 and a trailing side 116 at opposing ends along a longitudinal axis 117. Between the leading side 114 and trailing side 116 is an upper surface 118, a lower surface 120, an anterior side 122, a posterior side 124. The upper surface 118 and lower surface 120 are configured for contact with neighboring vertebrae. Each of the upper surface 118 and lower surface 120 may be one of, or a combination of, generally planar, concave, and convex.

Figure 9:
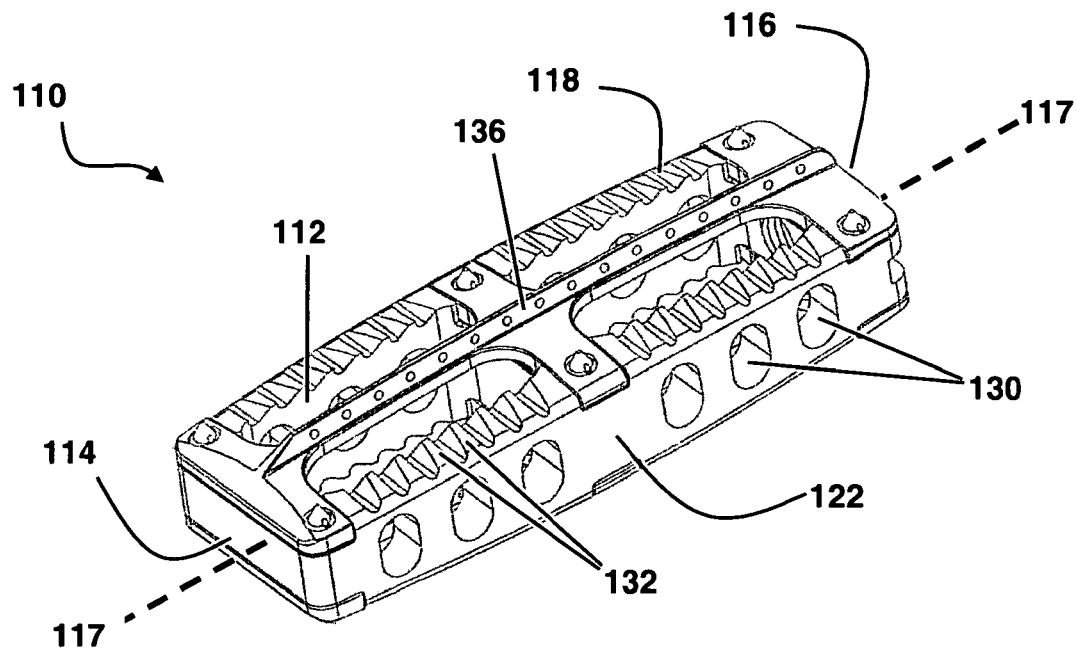
FIG. 9 is perspective view of a spinal fusion implant including a keel structure, according to a second embodiment of the present invention.
Figure 11:
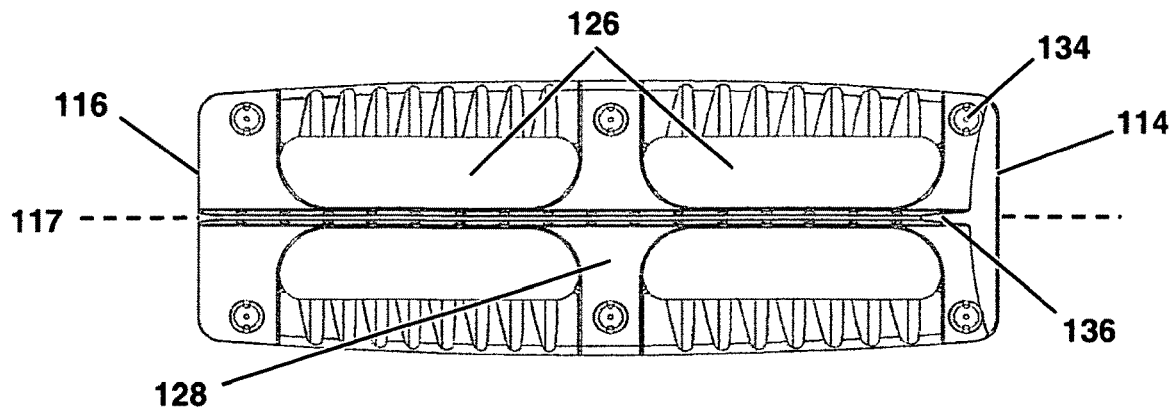
FIG. 11 is a top view of the fusion implant of FIG. 9.

The body 112 of the implant 110 may be configured with at least one large fusion aperture 126. As shown in FIG. 11, implant 110 has two large fusion apertures 126, separated by a medial support 128, extending between upper surface 118 and lower surface 120. The fusion apertures 126 function primarily as an avenue for bony fusion between adjacent vertebrae. Fusion apertures 126 may be provided in any of a variety of suitable shapes, including but not limited to the generally rectangular shape best viewed in FIG. 11, or a generally circular, oblong, polygonal, and/or triangular shape, or any combination thereof. The spinal fusion implant 110 may also have a plurality of visualization apertures 130, as illustrated in FIG. 9, extending between anterior side 122 and posterior side 124, which allow a user to assess the degree of bony fusion through visual observations (via X-ray, fluoroscopy, or other imaging technology), un-obscured by anterior side 122 or posterior side 124. The visualization apertures 130 may be provided in any of a variety of suitable shapes, including but not limited to the generally oblong shape best viewed in FIG. 15, or a generally circular, rectangular and/or triangular shape, or any combination thereof.

Figure 10:
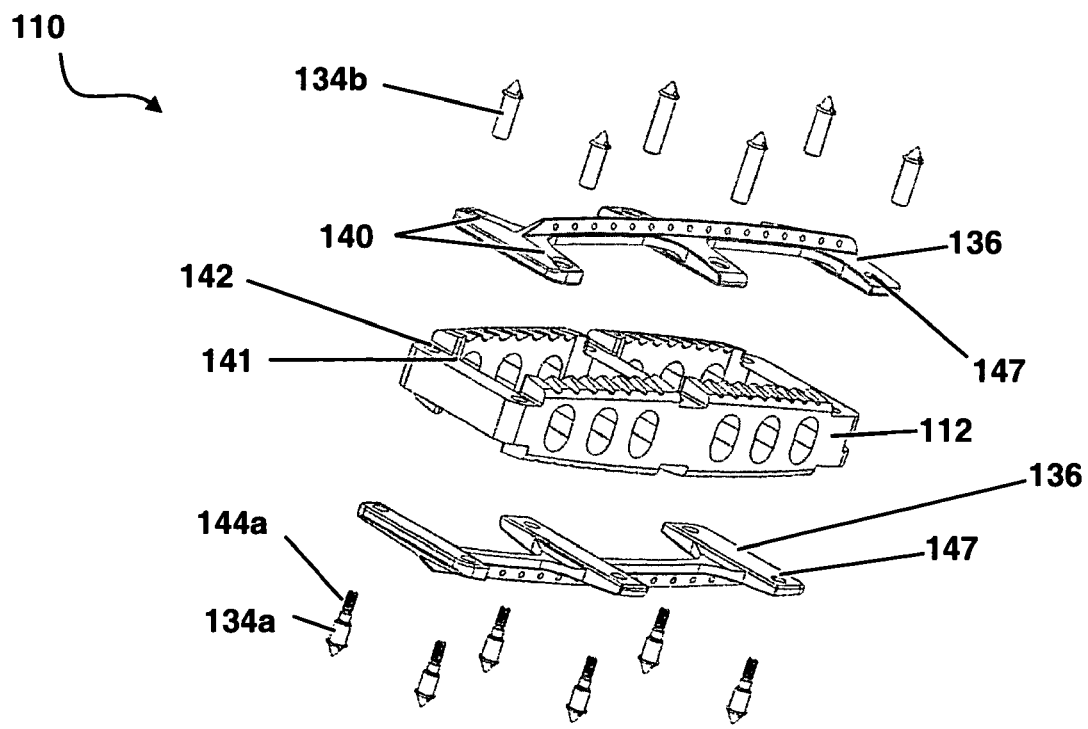
FIG. 10 is an exploded perspective view of the fusion implant of FIG. 9.

As best illustrated in FIG. 9, the fusion implant 110 may include anti-migration features designed to increase the traction between the spinal fusion implant 110 and the adjacent vertebral bodies, preventing movement or slippage of the implant 110 after implantation. Anti-migration features may include angled ridges 132 provided along the upper surface 118 and/or lower surface 120. The angled ridges 132 may be oriented such that they do not resist movement in the direction of insertion (i.e. the leading side 114 entering the intradiscal space first) but do resist movement in the opposing direction. This allows the implant 110 to be inserted without the need for excessive force that may cause damage to the vertebrae and/or the implant, while still preventing the implant from moving back along the path of insertion where natural barriers (e.g. the annulus fibrosis, or surrounding ligaments) were removed in order to access to the disc space for implant insertion. Other anti-migration features may include one or more spike members 134 disposed at various locations along the implant 110. By way of example, the implant 110 as illustrated includes a total of six spike members 134 disposed along each of the upper surface 118 and the lower surface 120. The spike members 134 may be manufactured from any of a variety of suitable materials, including but not limited to a metal, ceramic, and/or polymer material. Spike members 134 may be provided having radiopaque characteristics. When the spike members 134 are provided having radiodense characteristics and at least a portion of the implant 110 is manufactured from a radiolucent material (such as, by way of example only, PEEK and/or PEKK), the spike members 134 will be readily observable under X-ray or fluoroscopy such that a surgeon may track the progress of the implant 110 during implantation and/or the placement of the implant 110 after implantation. As illustrated in FIG. 10, the spike members 134 of implant 110 may comprise a male element 134a and a female element 134b which threadably engage each other through the implant body 112 and clamp keel structures 136 to the implant body 112.

Figure 12:
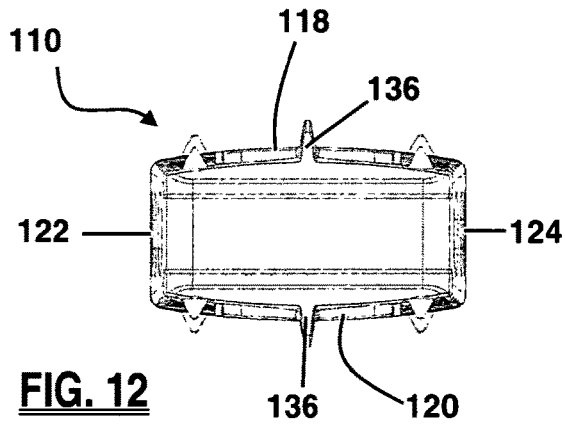
FIG. 12 is a frontal view of the leading side of the implant of FIG. 9.
Figure 13:
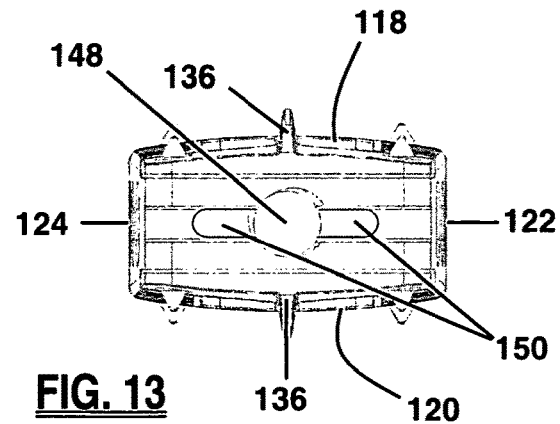
FIG. 13 is a back view of the trailing side of the implant of FIG. 9.
Figure 14:
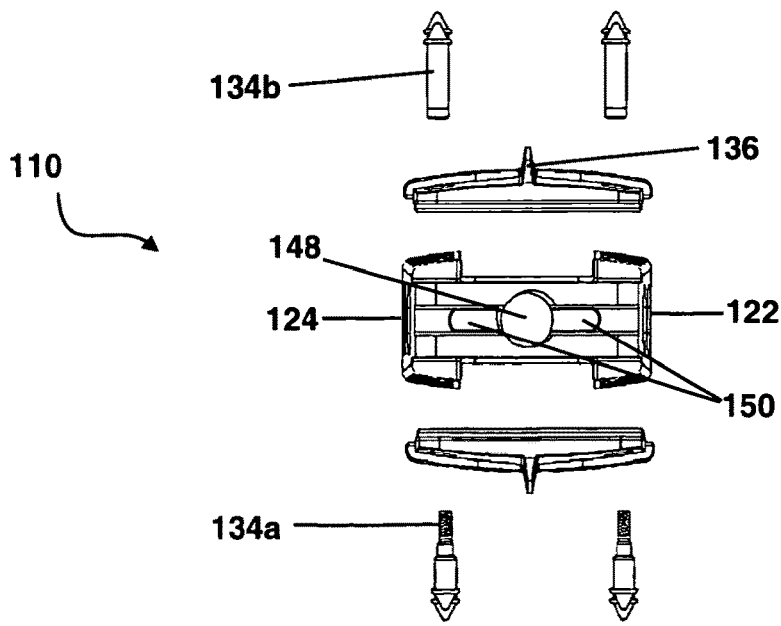
FIG. 14 is an exploded perspective view of the trailing side of the implant of FIG. 9.
Figure 15:
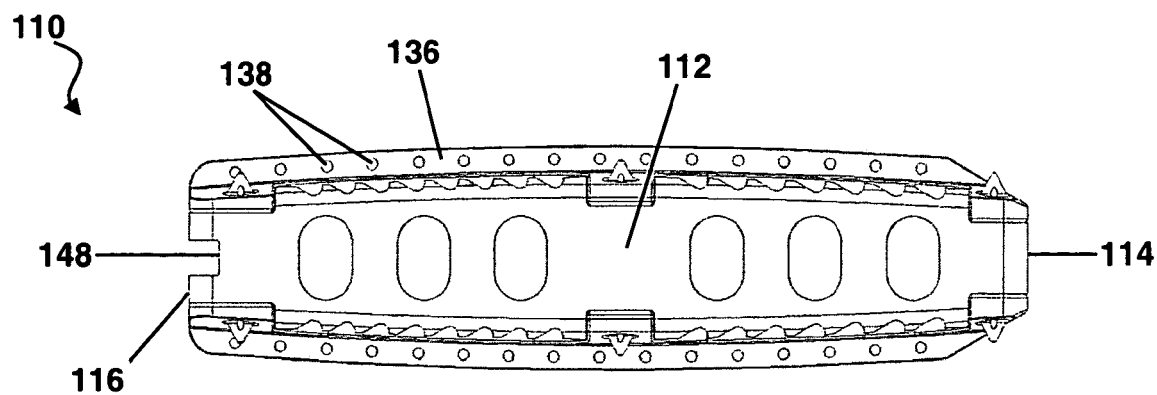
FIG. 15 is side view of the anterior side of the implant of FIG. 9.

As illustrated in FIGS. 11-13, additional members in the form of keel structures 136 augment the anti-migration features of implant 110 and further stabilize the position of the implant 110 within the disc space. Keel structures 136 may extend above the upper surface 118 and/or below the lower surface 120 along at least a portion of the longitudinal axis 117 of implant 110 between leading side 114 and trailing side 116. By way of example only, keel structures 136 may rise approximately 2.5 mm from the upper and/or lower surfaces 118, 120. Keel structures 136 may be positioned such that the keels run along the approximate centerline of implant 110. During implantation the keel structures 136 are inserted into keel channels formed in the adjacent vertebrae. As illustrated in FIG. 15, apertures 138 provided along the length of the keel, or a portion thereof, permit bony ingrowth through the keel structures. This serves to further integrate the implant 110 into the vertebrae. Alternatively (or in addition), the keel structures may be roughened and/or coated with bone growth promoting materials to further enhance the fusion process.

Figure 16:
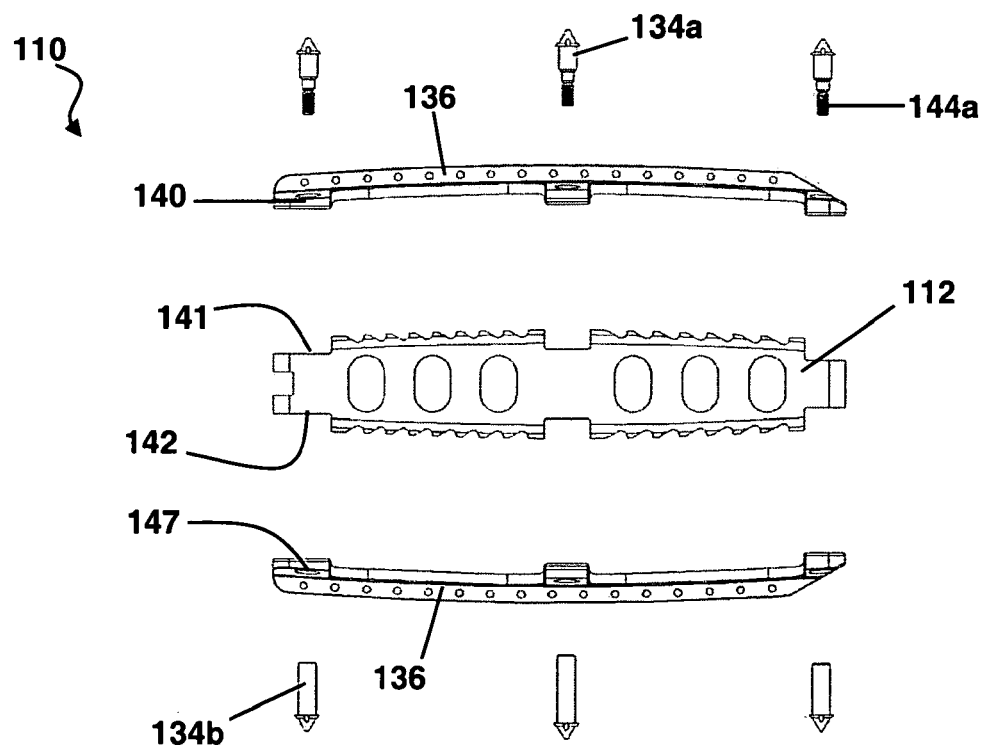
FIG. 16 is an exploded side view of the posterior side of the implant of FIG. 9.

The keel structures 136 can be made from the same material as implant body 112 or they can be made from a different material, or combination of materials. In this second embodiment, by way of example, the keel structures 136 are comprised of a metal (e.g. titanium) and the implant body is comprised of a polymer (e.g. PEEK or PEKK). It will be appreciated, however, that both the implant body 112 and keel structures 136 could be made from a polymer material, or both could be made of a metal material. Similarly, the implant body 112 and keel structures 136 may be formed as a single part, or as a combination of parts. By way of example, as best illustrated in FIG. 16, the implant 110 is formed by two keel structures 136 mated to the implant body 112 via spike members 134a and 134b. As best illustrated in FIG. 10, the keel structure includes a sextet of mating arms 140 configured to rest on mating shelves 141 of body 112. Spike bores 147 situated on the mating arms 140 are aligned with corresponding holes 142 formed through implant body 112. Female spike members 134b are placed through the holes 147 and 142 along one of the upper or lower surfaces 118, 120. From the opposite surface, male spike members 134a are then placed through the spike holes 147 and into an interior threaded portion (not shown) of female spike members 134b. As male spike members 134a are threaded into female spike members 134b, ridges 144a on male spike member 134a and ridges 144b on female spike member 134b engage the keel structures around spike bores 147 prevent the male spike member 134a and female spike member 134b from passing all the way through the keel structures and thus drawing and holding the keel structures and implant together as the male and female spike members are threadedly engaged to one another.

As illustrated in FIG. 15, the leading side 114 of implant 110 may include a slight taper to facilitate insertion of the implant 110 into the disc space between adjacent vertebrae. The trailing side 116 of implant 110 may possess mating structures configured for engagement with an insertion instrument (described below). According to the embodiment shown in FIGS. 13-15, the mating structures include a threaded receiving aperture 148 and a pair of grooved purchase regions 150 extending generally horizontally from either side of the receiving aperture 148. The receiving aperture 148 extends inwardly from the trailing side 116 in a generally perpendicular fashion relative to the trailing side 116 and is dimensioned to threadably receive a threaded connector 522 on the insertion instrument 500, as illustrated in FIG. 49 and described below. The grooved purchase regions 150 are dimensioned to receive corresponding distal head ridges 508 on the insertion instrument 500, which collectively provide an enhanced engagement between the implant 110 and insertion instrument 500. After keel channels have been formed in the vertebrae neighboring the affected disc space, the implant 110 is releasably attached to the insertion instrument 500, the keels 136 are aligned with the keel channels, and the implant inserted into position. Thereafter the insertion instrument is detached from the implant 110 and removed from the patient.

Figure 17:
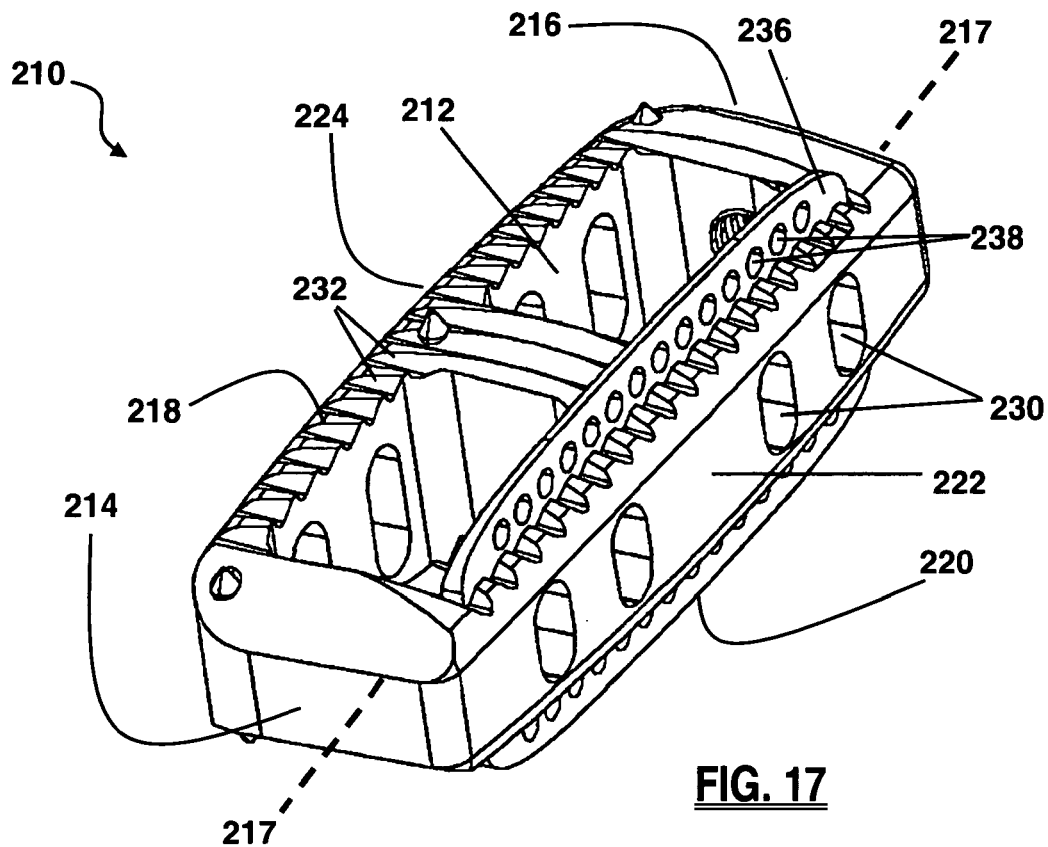
FIG. 17 is a perspective view of a spinal fusion implant with a keel structure, according to a third embodiment of the present invention.
Figure 18:
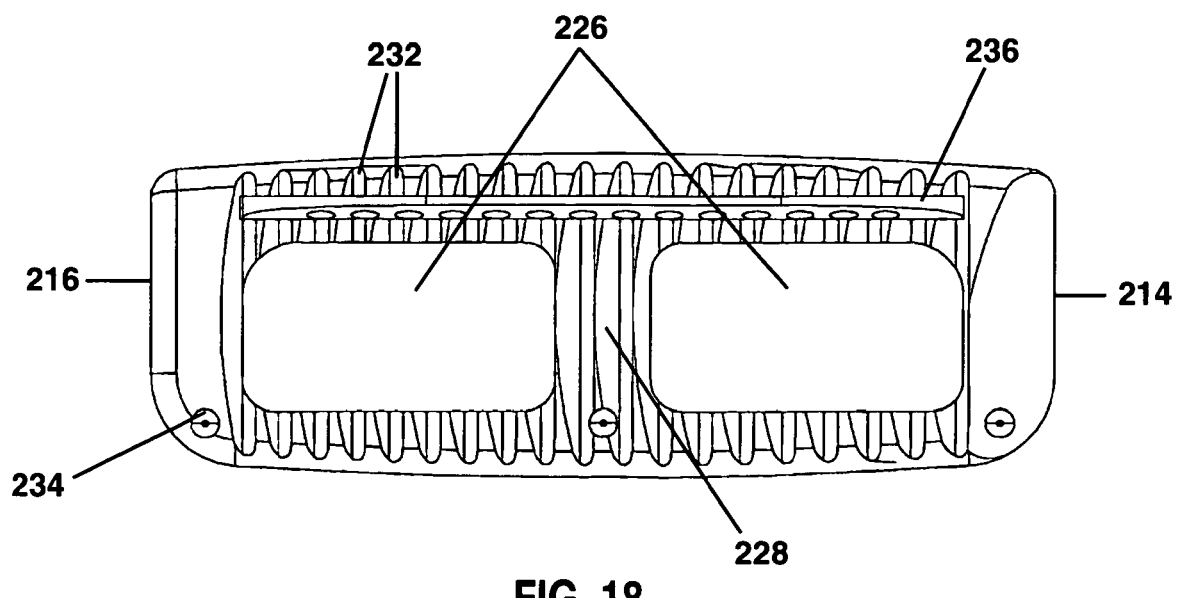
FIG. 18 is a top view of the fusion implant of FIG. 17.
Figure 19:
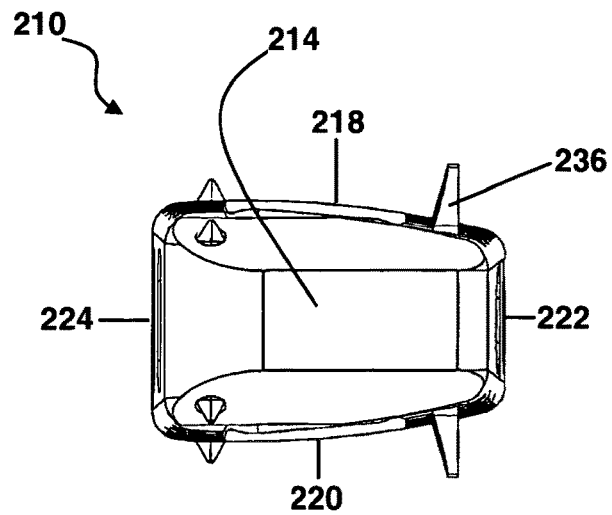
FIG. 19 is a frontal view of the leading side of the implant of FIG. 17.
Figure 20:
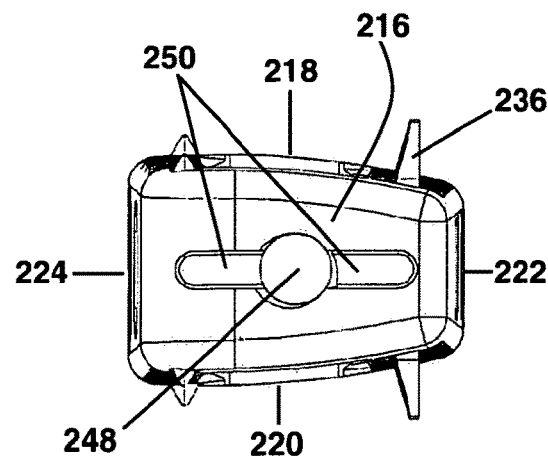
FIG. 20 is a back view of the trailing side of the implant of FIG. 17.

FIGS. 17-24 depict an example of a spinal fusion implant 210 according to a third embodiment of the present invention. The implant 210 generally comprises an implant body 212 and a keel structure 236. The implant body 212 has a leading side 214 and a trailing side 216 at opposing ends along a longitudinal axis 217. As best illustrated in FIGS. 19-20, between the leading side 214 and trailing side 216 is an upper surface 218, a lower surface 220, an anterior side 222, and a posterior side 224. The upper surface 218 and lower surface 220 are configured for contact with neighboring vertebrae. Each of the upper surface 218 and lower surface 220 may be one of, or a combination of, generally planar, concave, and convex. The anterior side 222 of the implant may possess a greater height dimension (not shown) than the posterior side 224, such that upper surface 218 and lower surface 220 converge toward one another at posterior side 224. By way of example only, the heights of anterior side 222 and posterior side 224 may be configured to provide a degree of curvature within a range of 1.degree.-20.degree.

An implant with this configuration (i.e. a taller anterior side) is tailored to accommodate the natural lordotic curvature found in the lumbar and cervical spine. It will be appreciated as within the scope of the present invention to provide an implant with a posterior side 224 possessing a greater height dimension than an anterior side 222, as illustrated in FIG. 19, so as to accommodate the natural kyphotic curvature of the thoracic spine. It should also be appreciated that the implant 210 may have anterior and posterior sides 222, 224 of equal height.

Figure 21:
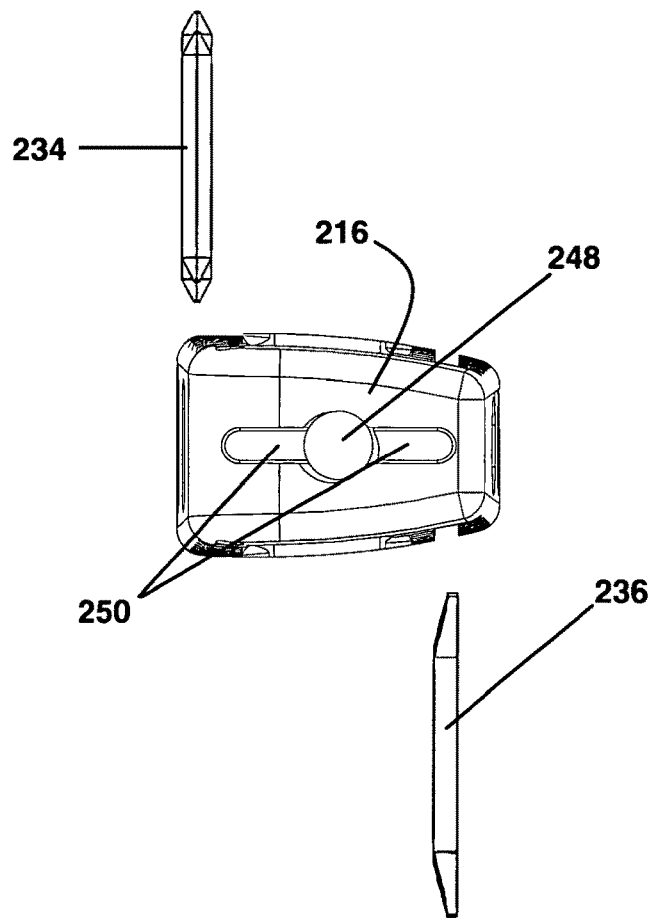
FIG. 21 is an exploded back view of the trailing side of the implant of FIG. 17.
Figure 22:
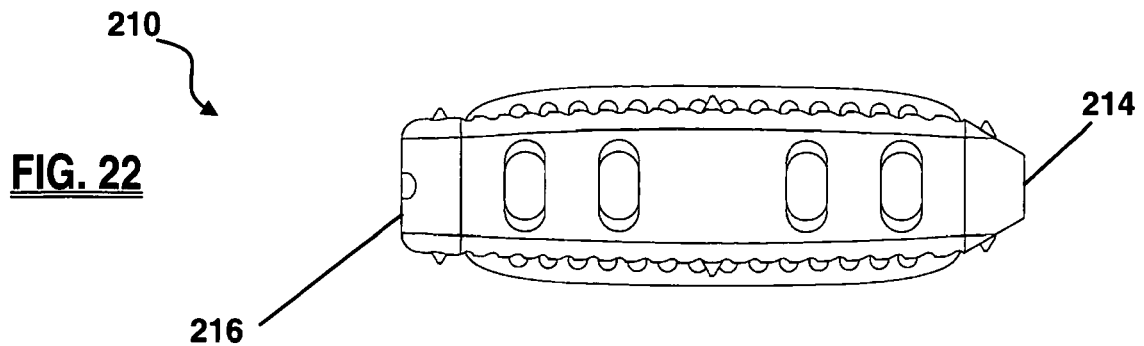
FIG. 22 is a side view of the anterior side of the implant of FIG. 17.
Figure 23:
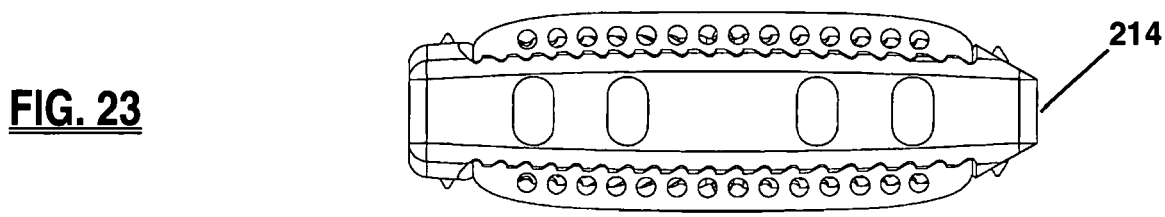
FIG. 23 is a side view of the posterior side of the implant of FIG. 17.
Figure 24:
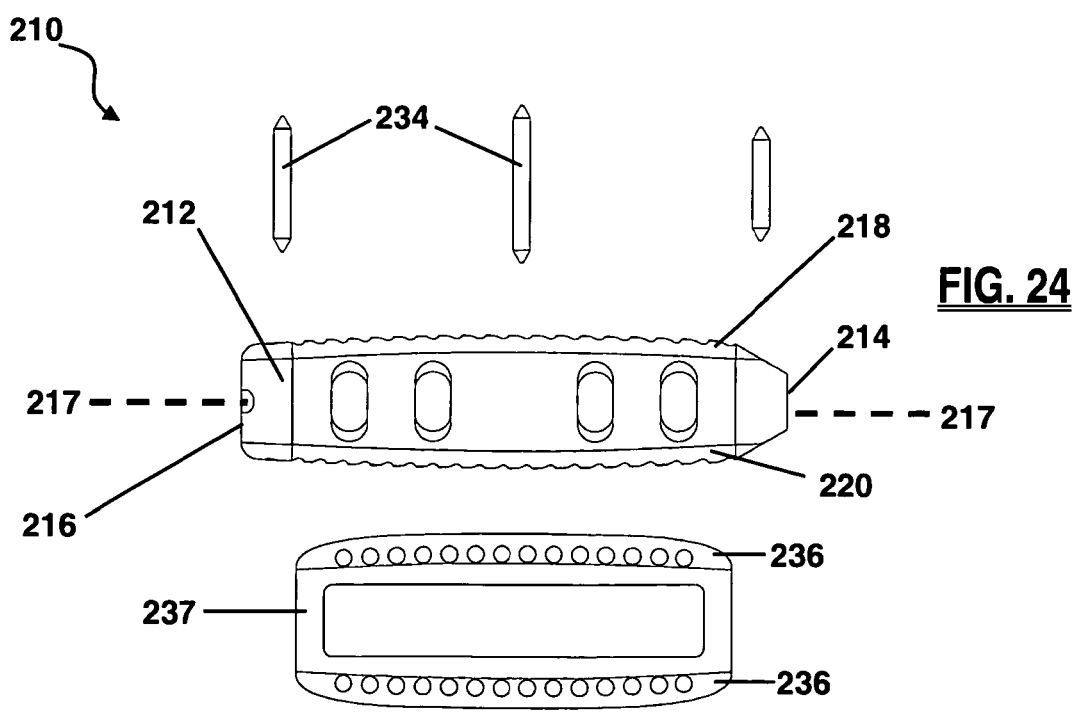
FIG. 24 is an exploded side view of the anterior side of the implant of FIG. 17.
Figure 25:
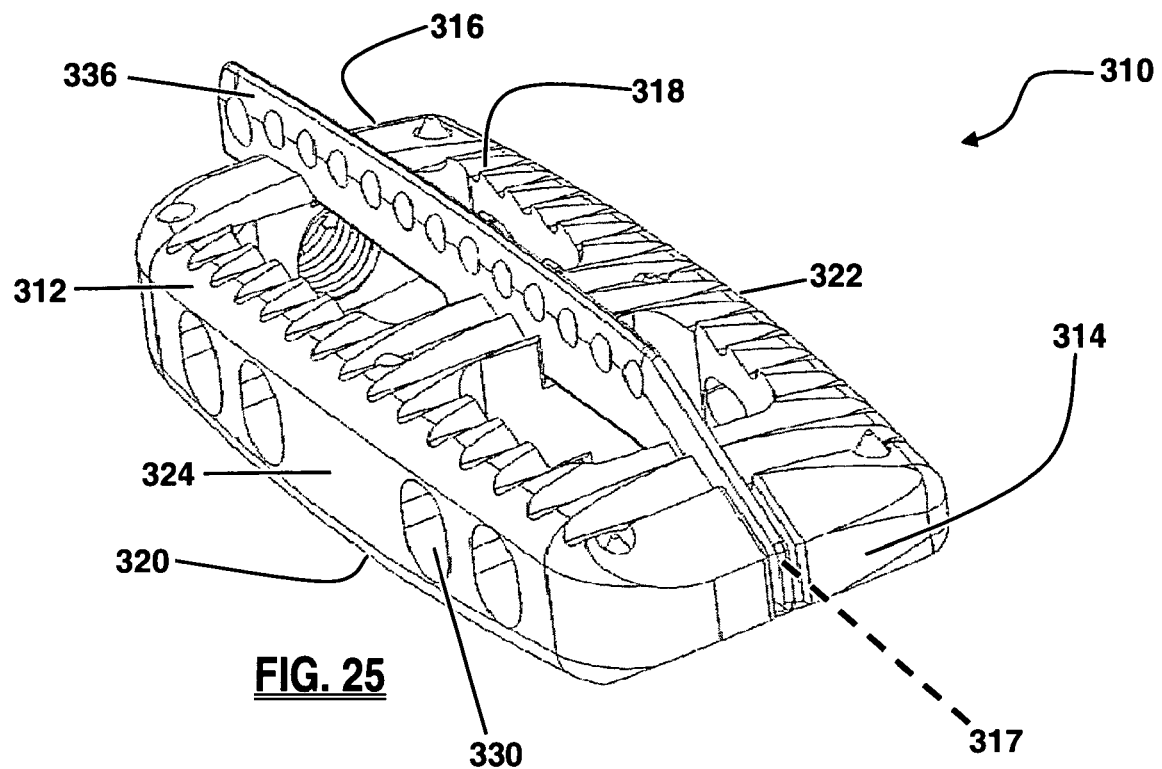
FIG. 25 is a perspective view of a spinal fusion implant with a keel structure, according to a fourth embodiment of the present invention.
Figure 26:
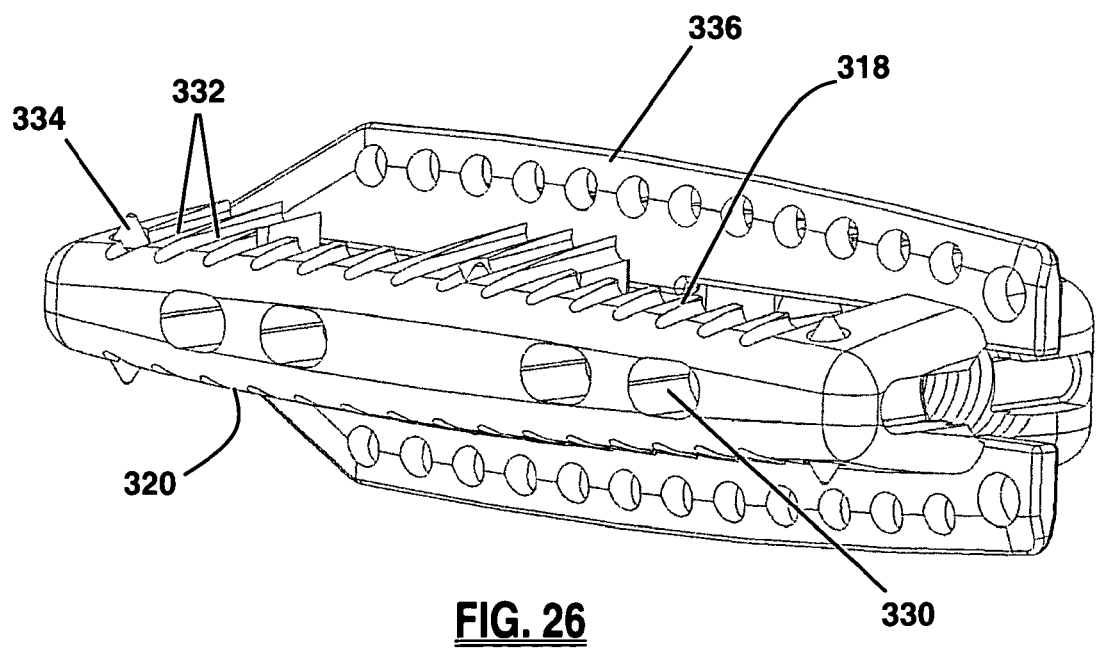
FIG. 26 is a perspective view of the trailing and anterior sides of the implant of FIG. 25.

As illustrated in FIGS. 22-24, the leading side 214 of implant 210 may include a slight taper to facilitate insertion of the implant 210 into the disc space between adjacent vertebrae. The trailing side 216 of implant 210 may possess mating structures configured for engagement with an insertion instrument (described below). As illustrated in FIGS. 20-21, the mating structures include a threaded receiving aperture 248 and a pair of grooved purchase regions 250 extending generally horizontally from either side of the receiving aperture 248. The receiving aperture 248 extends inwardly from the trailing side 216 in a generally perpendicular fashion relative to the trailing side 216 and is dimensioned to threadably receive a threaded connector 522 on the insertion instrument 500, as illustrated in FIG. 49 and described below. The grooved purchase regions 250 are dimensioned to receive corresponding distal head ridges 508 on the insertion instrument 500, which collectively provide an enhanced engagement between the implant 210 and insertion instrument 500.

As shown in FIG. 18, the body 212 of the implant 210 may be configured with at least one large fusion aperture 226. The implant 210 may have two large fusion apertures 226, separated by a medial support 228, extending in a vertical fashion between upper surface 218 and lower surface 220. The fusion apertures 226 function primarily as an avenue for bony fusion between adjacent vertebrae. Fusion apertures 226 may be provided in any of a variety of suitable shapes, including but not limited to the generally rectangular shape best viewed in FIG. 18, or a generally circular, oblong, polygonal, and/or triangular shape, or any combination thereof. The spinal fusion implant 210 may also have a plurality of visualization apertures 230 extending between the anterior side 222 and posterior side 224, which allow a user to assess the degree of bony fusion through visual observations (via X-ray, fluoroscopy, or other imaging technology), un-obscured by anterior side 222 or posterior side 224. The visualization apertures 230 may be provided in any of a variety of suitable shapes, including but not limited to the generally oblong shape best viewed in FIG. 17, or a generally circular, rectangular and/or triangular shape, or any combination thereof.

To protect against movement or slippage of the implant 210 after implantation, the fusion implant 210 may include anti-migration features designed to increase the traction between the spinal fusion implant 210 and the adjacent vertebral bodies. These anti-migration features may include angled ridges 232 provided along the upper surface 218 and/or lower surface 220. The angled ridges 232 may be oriented such that they do not resist movement in the direction of insertion (i.e. towards the leading end) but do resist movement in the opposing direction. This allows the implant 210 to be inserted without the need for excessive force that may cause damage to the vertebrae and/or the implant, while still preventing the implant from moving back along the path of insertion where natural barriers (e.g.

the annulus fibrosis, or surrounding ligaments) were removed in order to access to the disc space for implant insertion.

Additional anti-migration features in the form of keel structures 236 further stabilize the position of the implant 210 within the disc space. Keel structures 236 may extend above the upper surface 218 and/or below the lower surface 220 along at least a portion of the longitudinal axis 217 of implant 210 between leading side 214 and trailing side 216. By way of example only, keel structures 236 may rise approximately 2.5 mm from the upper and/or lower surfaces 218, 220. As best pictured in FIGS. 18-20, keel structures 236 may be canted and offset from the centerline of implant 210 such that they are positioned nearer to one of the anterior side 222 and posterior side 224 (not shown). During implantation, the keel structures 236 are inserted into keel channels formed in the adjacent vertebrae. As shown in FIG. 17, apertures 238 provided along the length of the keel, or a portion thereof, permit bony ingrowth through the keel structures. This serves to further integrate the implant 210 into the vertebrae. Alternatively (or in addition), the keel structures may be roughened and/or coated with bone growth promoting materials to further enhance the fusion process.

As illustrated in FIGS. 18 and 24, other anti-migration features may include one or more spike members 234 disposed at various locations along the implant 210. The implant 210 may include a total of three spike members 234 extending between the upper surface 218 and the lower surface 220. The spike members 234 may be manufactured from any of a variety of suitable materials, including but not limited to a metal, ceramic, and/or polymer material. Spike members 234 may be provided having radiopaque characteristics. When the spike members 234 are provided having radiodense characteristics and at least a portion of the implant 210 is manufactured from a radiolucent material (such as, by way of example only, PEEK and/or PEKK), the spike members 234 will be readily observable under X-ray or fluoroscopy such that a surgeon may track the progress of the implant 210 during implantation and/or the placement of the implant 210 after implantation. Spike members 234 each comprise a unitary element extending through the upper surface 218 and lower surface 220 (best viewed in FIGS. 21 and 24). Alternatively, each spike member 234 could comprise a shorter element which only extends through a single surface (not shown).

The keel structures 236 can be made from the same material as implant body 212 or they can be made from a different material, or combination of materials. In this third embodiment, by way of example, the keel structures 236 are comprised of a metal (e.g. titanium) and the implant body is comprised of a polymer (e.g. PEEK or PEKK). It will be appreciated that both the implant body 212 and keel structures 236 could be made from a polymer material, or both could be made of a metal material. Similarly, the implant body 212 and keel structures 236 may be formed as a single part, or as a combination of parts. By way of example only, as shown in FIG. 24, the implant 210 may be formed by injection molding the implant body 212 to surround a keel frame 237 having two keel structures 236.

As illustrated in FIGS. 22-24, the leading side 214 of implant 210 may be tapered to facilitate insertion of the implant 210 into the disc space between adjacent vertebrae. As shown in FIGS. 20-21, the trailing side 216 of implant 210 may possess mating structures configured for engagement with an insertion instrument (described below). According to the embodiment shown, the mating structures include a threaded receiving aperture 248 and a pair of grooved purchase regions 250 extending generally horizontally from either side of the receiving aperture 248. The receiving aperture 248 extends inwardly from the trailing side 216 in a generally perpendicular fashion relative to the trailing side 216 and is dimensioned to threadably receive a threaded connector 522 on the insertion instrument 500 described below. The grooved purchase regions 250 are dimensioned to receive corresponding distal head ridges 508 on the insertion instrument 500, as shown in FIG. 49, which collectively provide an enhanced engagement between the implant 110 and insertion instrument 500. After keel channels have been formed in the vertebrae neighboring the affected disc space, the implant 210 is releasably attached to the insertion instrument 500, the keels 236 are aligned with the keel channels, and the implant inserted into position. Thereafter the insertion instrument is detached from the implant 210 and removed from the patient.

FIGS. 25-32 depict an example of a spinal fusion implant 310 according to a fourth embodiment of the present invention. The implant 310 generally comprises an implant body 312 and a keel structure 336. The implant body 312 has a leading side 314 and a trailing side 316 at opposing ends along a longitudinal axis 317. Between the leading side 314 and trailing side 316 is an upper surface 318, a lower surface 320, an anterior side 322, a posterior side 324. The upper surface 318 and lower surface 320 are configured for contact with neighboring vertebrae. Each of the upper surface 318 and lower surface 320 may be one of, or a combination of, generally planar, concave, and convex. The anterior side 322 of the implant may possess a greater height dimension (not shown) than the posterior side 324, such that upper surface 318 and lower surface 320 converge toward one another at posterior side 324. By way of example only, the heights of anterior side 322 and posterior side 324 may be configured to provide a degree of curvature within a range of 1.degree.-20.degree. An implant with this configuration (i.e. a taller anterior side) is tailored to accommodate the natural lordotic curvature found in the lumbar and cervical spine. It will be appreciated as within the scope of the present invention to provide an implant with a posterior side 324 possessing a greater height dimension than an anterior side 322 so as to accommodate the natural kyphotic curvature of the thoracic spine. It should also be appreciated that the implant 310 may have anterior and posterior sides 322, 324 of equal height.

Figure 28:
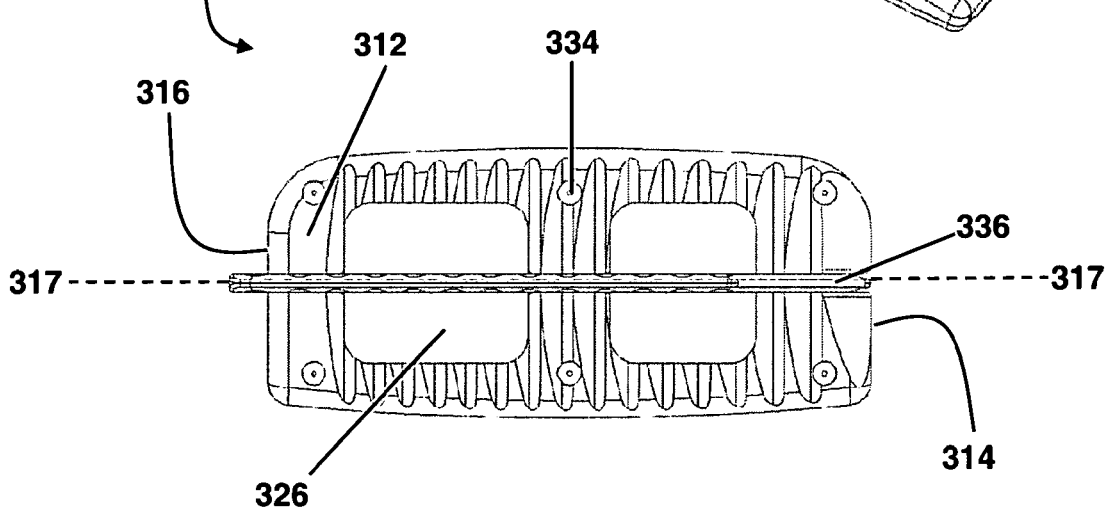
FIG. 28 is a top view of the implant of FIG. 25.
Figure 29:
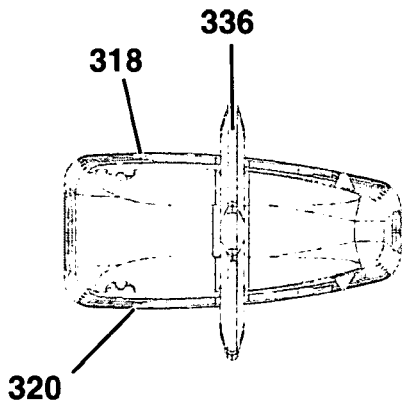
FIG. 29 is a front view of the leading side of FIG. 25.

As shown in FIG. 28, the body 312 of the implant 310 may be configured with at least one large fusion aperture 326. Implant 310 has two large fusion apertures 326, separated by a medial support 328, extending in a vertical fashion between upper surface 318 and lower surface 320. The fusion apertures 326 function primarily as an avenue for bony fusion between adjacent vertebrae. Fusion apertures 326 may be provided in any of a variety of suitable shapes, including but not limited to the generally rectangular shape and generally square shape best viewed in FIG. 28, or a generally circular, oblong, polygonal, and/or triangular shape, or any combination thereof. The spinal fusion implant 310 may also have a plurality of visualization apertures 330 extending between the anterior side 322 and posterior side 324, which allow a user to assess the degree of bony fusion through visual observations (via X-ray, fluoroscopy, or other imaging technology), un-obscured by anterior side 322 or posterior side 324. The visualization apertures 330 may be provided in any of a variety of suitable shapes, including but not limited to the generally oblong shape best viewed in FIG. 25, or a generally circular, rectangular and/or triangular shape, or any combination thereof.

To protect against movement or slippage of the implant 310 after implantation, the fusion implant 310 may include anti-migration features designed to increase the traction between the spinal fusion implant 310 and the adjacent vertebral bodies. These anti-migration features, best viewed in FIG. 26, may include angled ridges 332 provided along the upper surface 318 and/or lower surface 320. The angled ridges 332 may be oriented such that they do not resist movement in the direction of insertion (i.e. towards the leading end) but do resist movement in the opposing direction. This allows the implant 310 to be inserted without the need for excessive force that may cause damage to the vertebrae and/or the implant, while still preventing the implant from moving back along the path of insertion where natural barriers (e.g. the annulus fibrosis, or surrounding ligaments) were removed in order to access to the disc space for implant insertion. Other anti-migration features may include one or more spike members 334 disposed at various locations along the implant 310. The implant 310 may include a total of six spike members 334 extending between the upper surface 318 and the lower surface 320. The spike members 334 may be manufactured from any of a variety of suitable materials, including but not limited to a metal, ceramic, and/or polymer material. Spike members 334 may be provided having radiopaque characteristics. When the spike members 334 are provided having radiodense characteristics and at least a portion of the implant 310 is manufactured from a radiolucent material (such as, by way of example only, PEEK and/or PEKK), the spike members 334 will be readily observable under X-ray or fluoroscopy such that a surgeon may track the progress of the implant 310 during implantation and/or the placement of the implant 310 after implantation. Spike members 334 may each comprise a unitary element extending through the upper surface 318 and lower surface 320. Alternatively, each spike member 334 could comprise a shorter element which only extends through a single surface (not shown).

Additional members in the form of keel structures 336 augment the anti-migration features of implant 310 and further stabilize the position of the implant 310 within the disc space. Keel structures 336 may extend above the upper surface 318 and/or below the lower surface 320 along at least a portion of the longitudinal axis 317 of implant 310 between leading side 314 and trailing side 316. By way of example only, keel structures 336 may rise approximately 2.5 mm from the upper and/or lower surfaces 318, 320. As best pictured in FIGS. 28-30, keel structures 336 may be positioned along the centerline of implant 310. During implantation the keel structures 336 are inserted into keel channels formed in the adjacent vertebrae. Apertures 338 provided along the length of the keel, or a portion thereof, permit bony ingrowth through the keel structures. This serves to further integrate the implant 310 into the vertebrae. Alternatively (or in addition), the keel structures may be roughened and/or coated with bone growth promoting materials to further enhance the fusion process.

Figure 27:
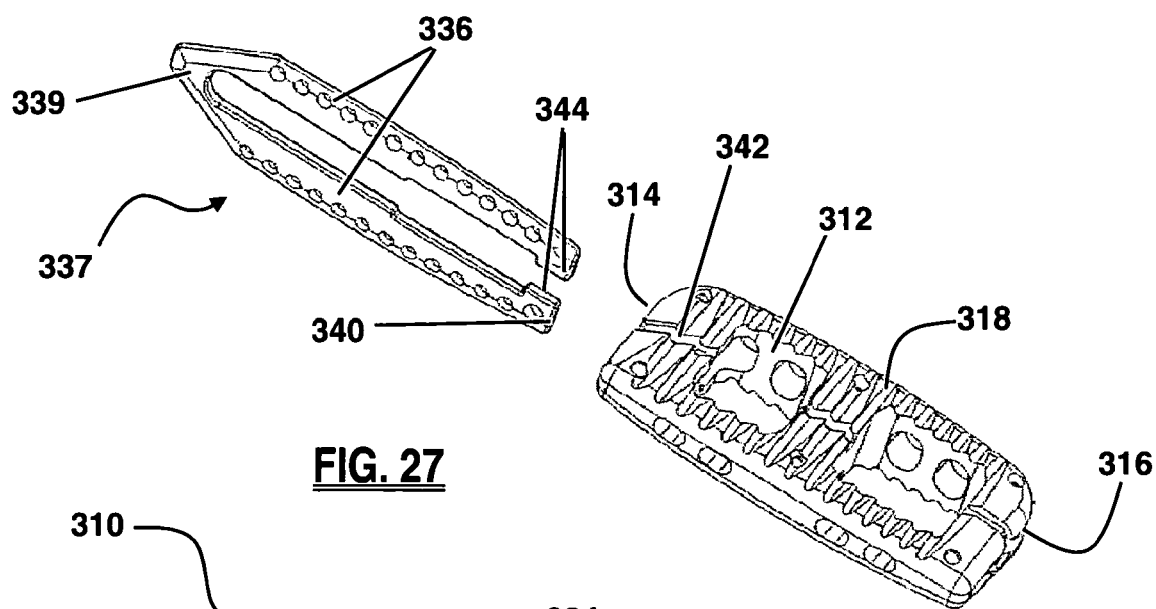
FIG. 27 is a perspective top view of the implant of FIG. 25.
Figure 31:
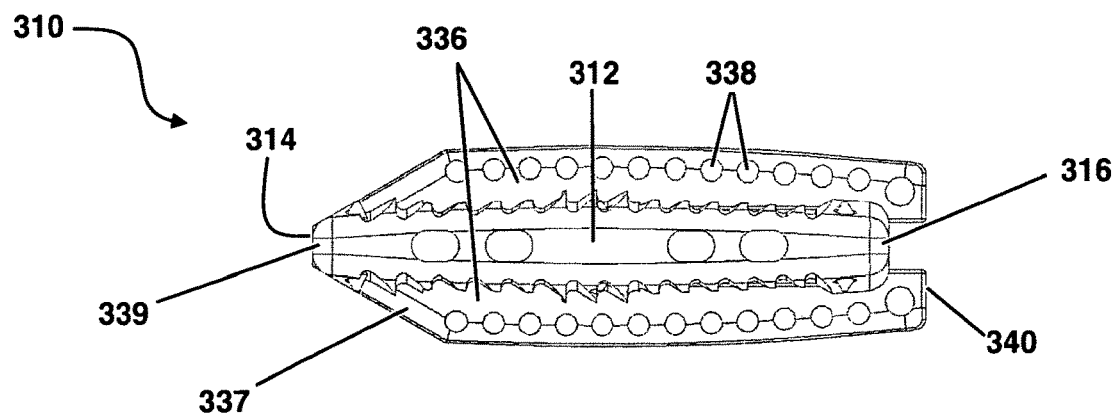
FIG. 31 is a side view of the anterior side of FIG. 25.
Figure 32:
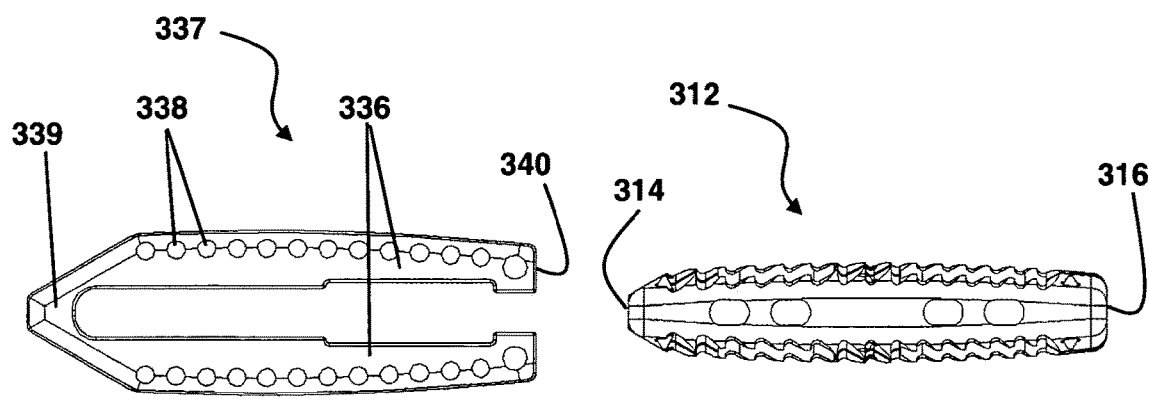
FIG. 32 is a side view of the posterior side of FIG. 25.
Figure 33:
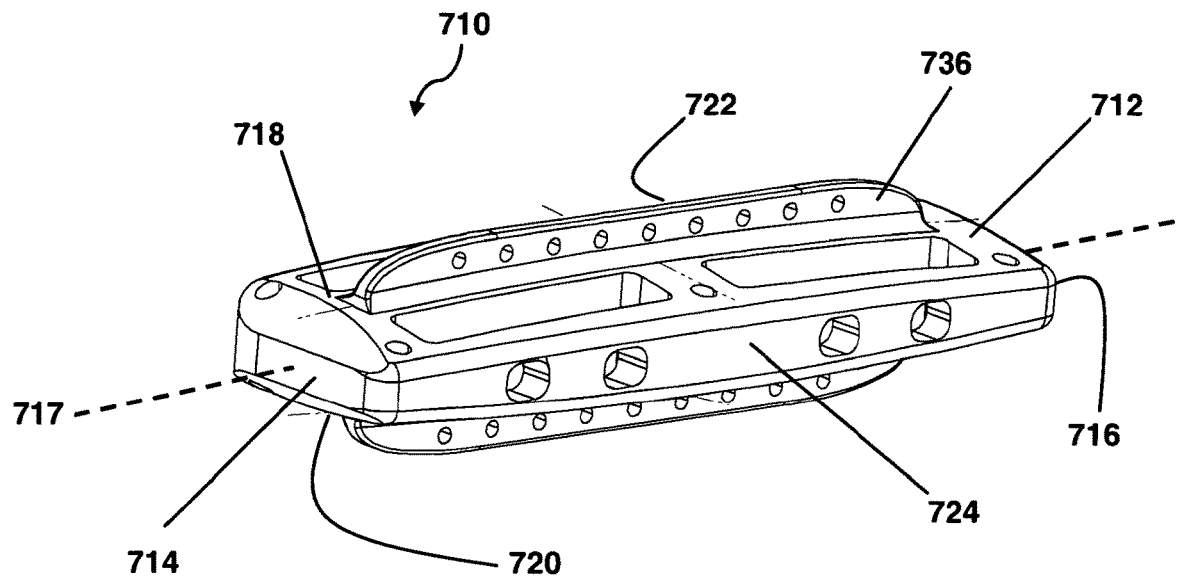
FIG. 33 is a perspective view of a spinal fusion implant with a keel, according to a fifth embodiment of the present invention.

The keel structures 336 can be made from the same material as implant body 312 or they can be made from a different material, or combination of materials. In this fourth embodiment, by way of example, the keel structures 336 are comprised of a metal (e.g. titanium) and the implant body is comprised of a polymer (e.g. PEEK or PEKK). It will be appreciated that both the implant body 312 and keel structures 336 could be made from a polymer material, or both could be made of a metal material. Similarly, the implant body 312 and keel structures 336 may be formed as a single part, or as a combination of parts. By way of example only, as shown in FIGS. 31-32, the implant 310 is formed by a keel frame 337 that is snap-fit around the implant body 312. According to one method of use, the keel frame may be inserted into position within keel channels formed in the vertebrae and thereafter the implant body 312 may be inserted into the keel frame 337. The keel frame 337 comprises two keel structures 336 attached via a tapered leading end 339. The keel structures 336 are unattached at the trailing end 340 such that the keel structures 336 can flex to allow passage of the implant body 312 into the frame 337. As shown in FIG. 27, an attachment groove 342 is disposed along the upper surface 318 and lower surface 320 from leading side 314 to trailing side 316. When attached, the interior edges of the keel structures 336 and the interior portion of the leading end 339 are captured in the attachment groove 342. Tabs 344 on the trailing end 340 snap around the edges of the trailing side 316 and prevent the implant body 312 from backing out of the keel frame 337.

Figure 30:
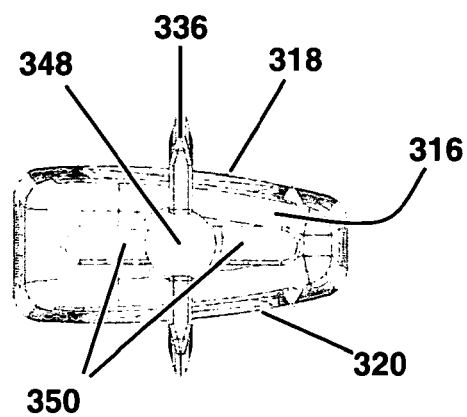
FIG. 30 is a back view of the trailing side of FIG. 25.
Figure 50:
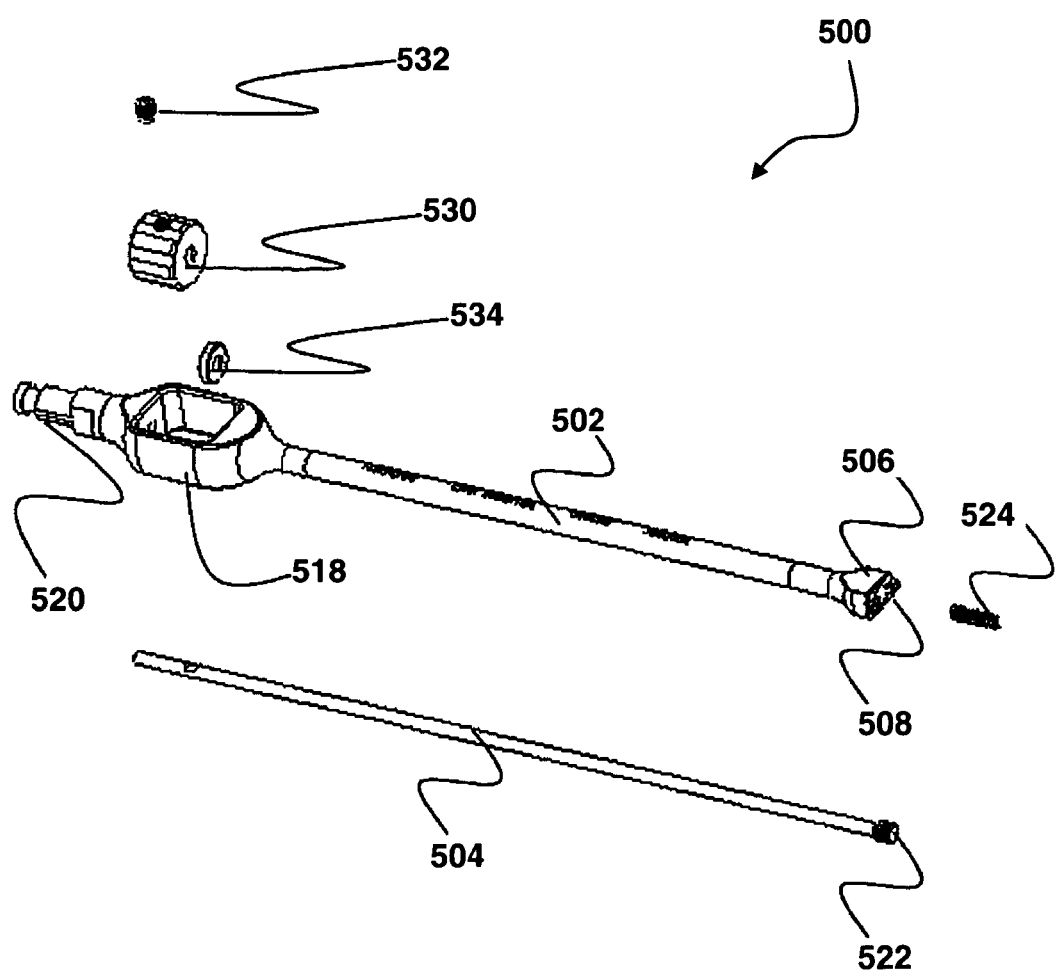
FIG. 50 is an exploded perspective view of the insertion instrument of the insertion instrument of FIG. 48.

As illustrated in FIGS. 31-32, the leading side 314 of implant 310 may be tapered to facilitate insertion of the implant 310 into the disc space between adjacent vertebrae. As shown in FIG. 30, the trailing side 316 of implant 310 may possess mating structures configured for engagement with an insertion instrument. According to the embodiment shown, the mating structures include a threaded receiving aperture 348 and a pair of grooved purchase regions 350 extending generally horizontally from either side of the receiving aperture 348. The receiving aperture 348 extends inwardly from the trailing side 316 in a generally perpendicular fashion relative to the trailing side 316 and is dimensioned to threadably receive a threaded connector 522 on the insertion instrument 500, as shown in FIGS. 49-50, described below. The grooved purchase regions 350 are dimensioned to receive corresponding distal head ridges 508, as shown in FIG. 49, on the insertion instrument 500, which collectively provide an enhanced engagement between the implant 310 and insertion instrument 500. After keel channels have been formed in the vertebrae neighboring the affected disc space, the implant 310 is releasably attached to the insertion instrument 500. Next, the keels 336 are aligned with the keel channels, and the implant 310 inserted into position. Thereafter the insertion instrument is detached from the implant 310 and removed from the surgical corridor, leaving the implant 310 in place between the vertebrae. Alternatively, the keel frame 337 may be inserted into the keel channels prior to insertion of the implant 310. With the keel frame in position, the implant may be aligned with the keel frame and thereafter advanced into position until the implant snaps completely into the keel frame.

FIGS. 33-38 depict an example of a spinal fusion implant 710 according to a fifth embodiment of the present invention. The implant 710 generally comprises an implant body 712 and a keel structure 736. The implant body 712 has a leading side 714 and a trailing side 716 at opposing ends along a longitudinal axis 717. Between the leading side 714 and trailing side 716 are an upper surface 718, a lower surface 720, an anterior side 722, and a posterior side 724. To maintain the disc space according to the natural curvature of the spine, the anterior side 722 of the implant may possess a greater height dimension than the posterior side 724, such that upper surface 718 and lower surface 720 converge toward one another at posterior side 724. By way of example only, the heights of anterior side 722 and posterior side 724 may be configured to provide a degree of curvature within a range of 1.degree.-20.degree. An implant with this configuration (i.e. a taller anterior side) is tailored to accommodate the natural lordotic curvature found in the lumbar and cervical spine. In another embodiment (not shown), an implant 710 may have a posterior side 724 possessing a greater height dimension than an anterior side 722 so as to accommodate the natural kyphotic curvature of the thoracic spine. The implant 710 may also have anterior and posterior sides 722, 724 of equal height. Each of the upper surface 718 and lower surface 720 may be one of, or a combination of, generally planar, concave, and convex.

Figure 35:
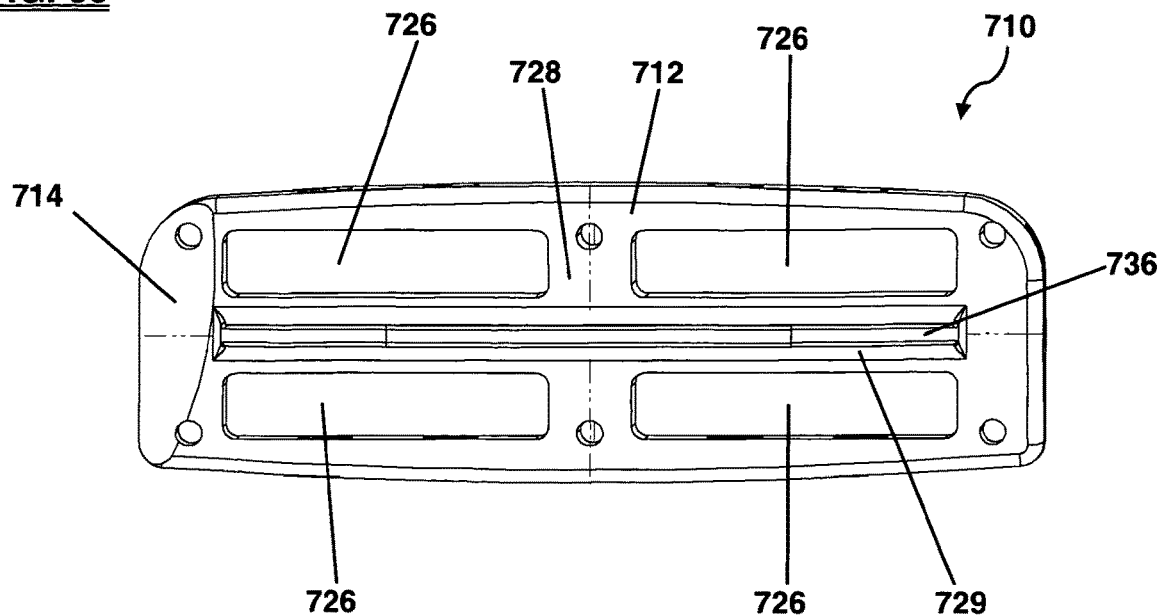
FIG. 35 is a top view of the implant of FIG. 33.
Figure 36:
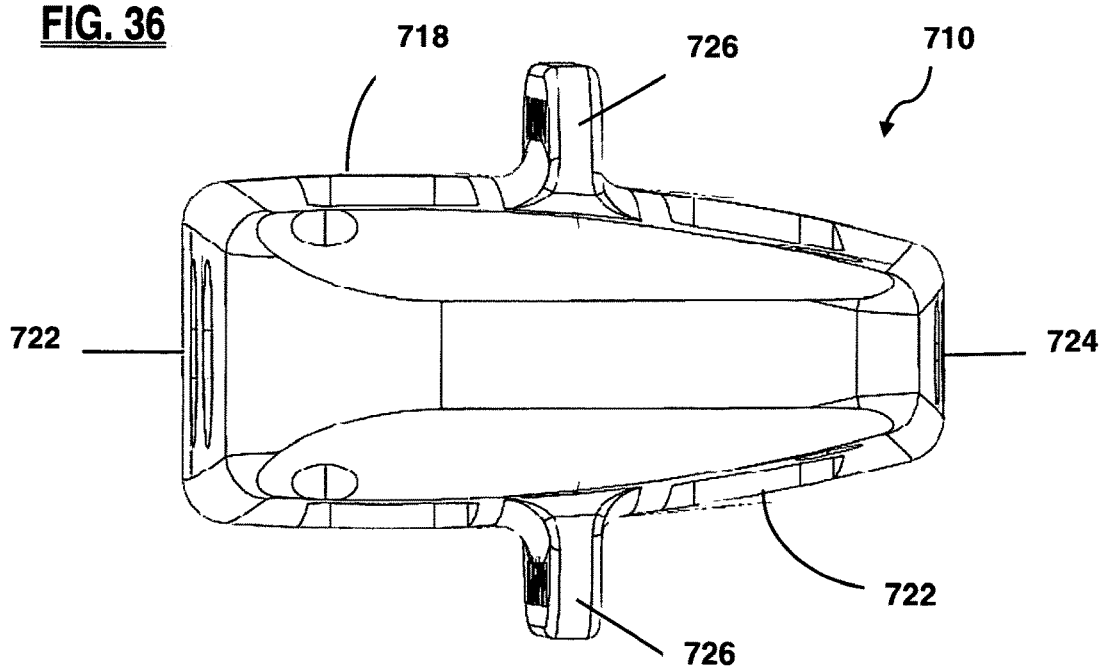
FIG. 36 is a front view of the leading side of the implant of FIG. 33.

As illustrated in FIG. 35, the body 712 of the implant 710 may be configured with at least one large fusion aperture 726. As shown, implant 710 has four fusion apertures 726, separated by a medial support 728 and a lateral support 729, each extending in a vertical fashion between upper surface 718 and lower surface 720. The fusion apertures 726 function primarily as an avenue for bony fusion between adjacent vertebrae. Fusion apertures 726 may be provided in any of a variety of suitable shapes, including but not limited to the generally rectangular shape best viewed in FIG. 35 or a generally circular, oblong, polygonal, and/or triangular shape, or any combination thereof. The spinal fusion implant 710 may also have a plurality of visualization apertures 730 extending between the anterior side 722 and posterior side 724, which allow a user to assess the degree of bony fusion through visual observations (via X-ray, fluoroscopy, or other imaging technology), un-obscured by anterior side 722 or posterior side 724. The visualization apertures 730 may be provided in any of a variety of suitable shapes, including but not limited to the generally oblong shape best viewed in FIGS. 45 and 47, or a generally circular, rectangular and/or triangular shape, or any combination thereof.

Figure 34:
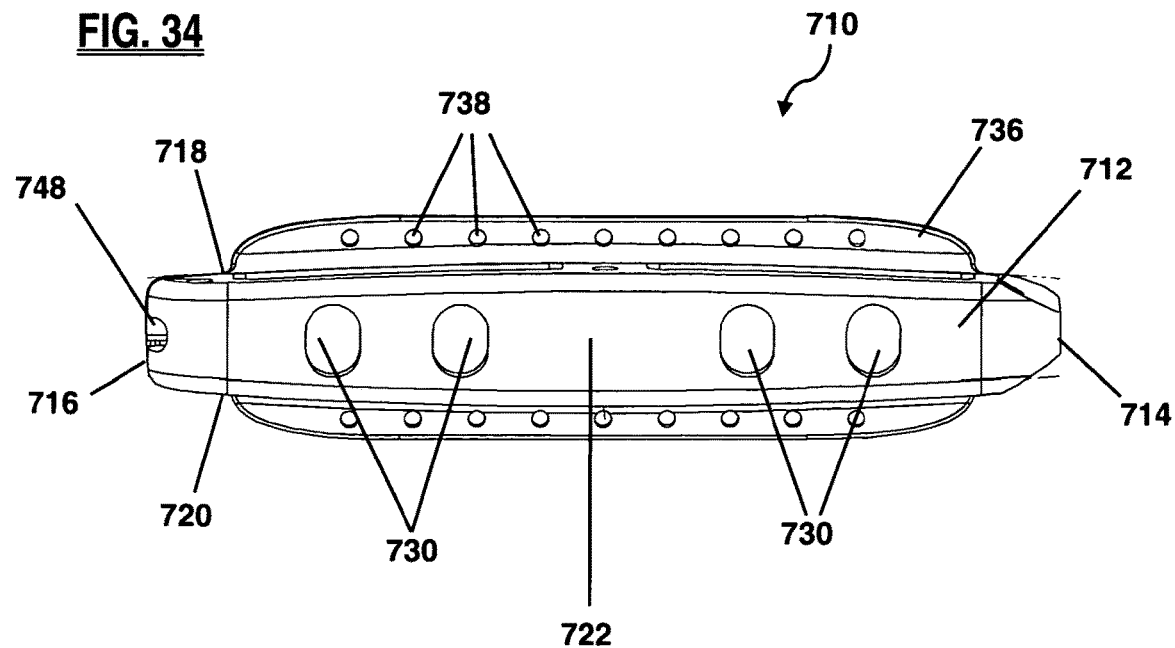
FIG. 34 is a side view of the anterior side of the implant of FIG. 33.

As illustrated in FIGS. 33-38, keel structures 736 may extend above the upper surface 718 and/or below the lower surface 720 along at least a portion of the longitudinal axis 717 of implant 710 between leading side 714 and trailing side 716. By way of example only, keel structures may rise approximately 2.5 mm from the upper and/or lower surfaces 718, 720. During implantation the keel structures 736 are inserted into keel channels formed in the adjacent vertebrae. As illustrated in FIG. 34, apertures 738 provided along the length of the keel, or a portion thereof, permit bony ingrowth through the keel structures. This serves to further integrate the implant 710 into the vertebrae and to stabilize the position of the implant 710 within the disc space. Alternatively (or in addition), the keel structures may be roughened and/or coated with bone growth promoting materials to further enhance the fusion process. The keel structures 736 are preferably composed from the same material as implant body 712. By way of example, the keel structures 736 and the implant body 712 are comprised of a polymer (e.g. PEEK or PEKK). The keel structures 736 and implant body 712 are preferably formed together as one unit, and may be formed, for example, by machining or molding.

Figure 37:
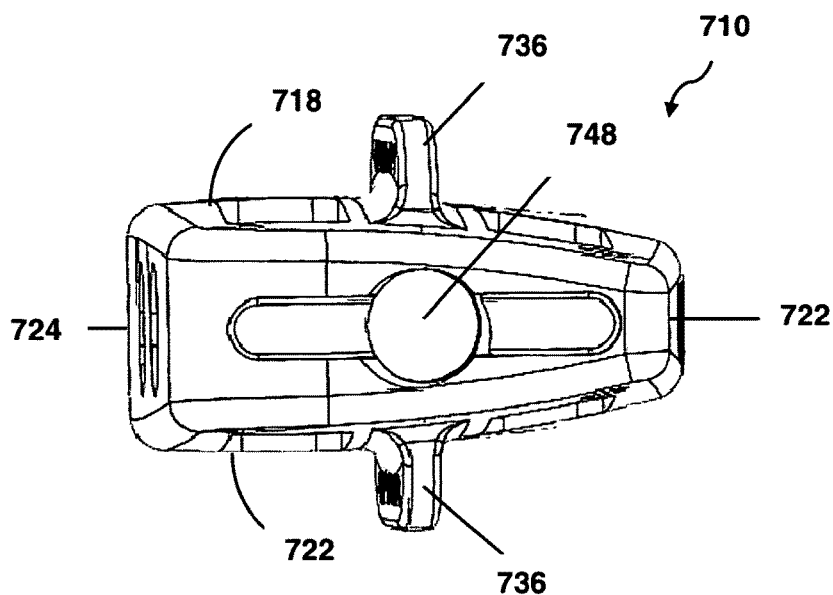
FIG. 37 is a back view of the trailing side of the implant of FIG. 33.
Figure 38:
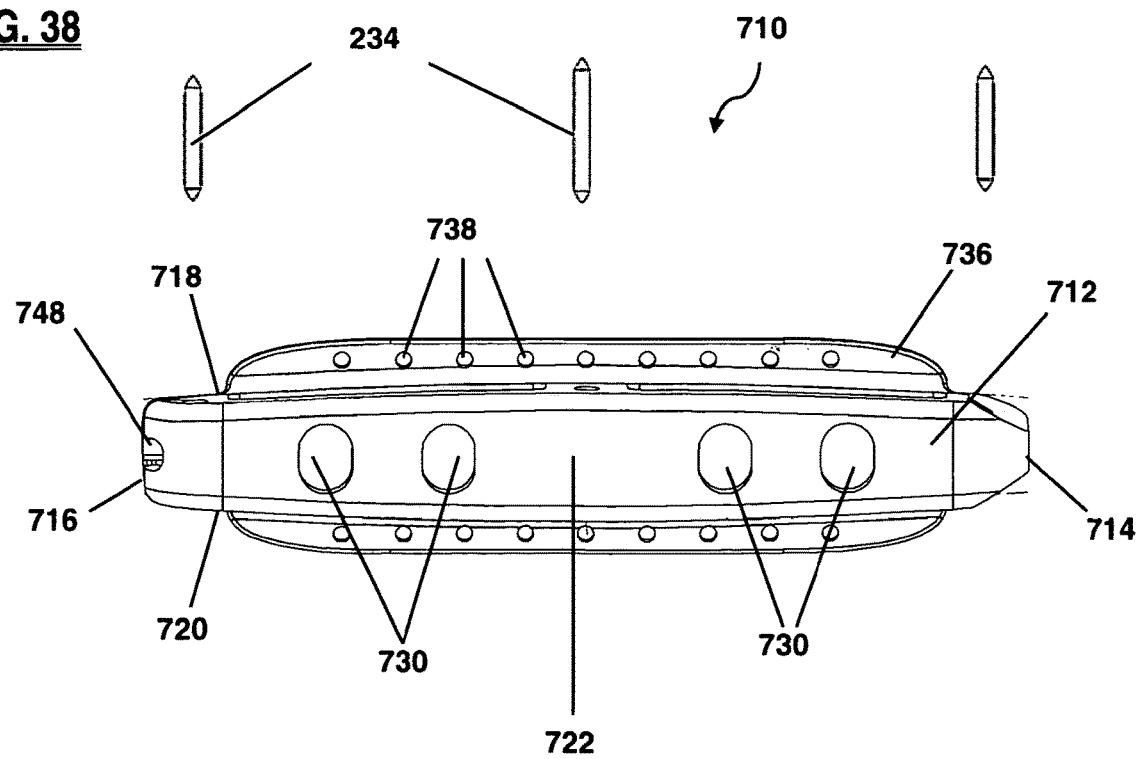
FIG. 38 is an exploded side view of the anterior side of the implant of FIG. 33.

As illustrated in FIG. 34, the leading side 714 of implant 710 may be tapered to facilitate insertion of the implant 710 into the disc space between adjacent vertebrae. As shown in FIG. 37, the trailing side 716 of implant 710 may possess mating structures configured for engagement with an insertion instrument. According to the embodiment shown, the mating structures include a threaded receiving aperture 748. The receiving aperture 748 extends inwardly from the trailing side 716 in a generally perpendicular fashion relative to the trailing side 716 and is dimensioned to threadably receive a threaded connector 522 on the insertion instrument 500, as shown in FIG. 49. After keel channels have been formed in the vertebrae neighboring the affected disc space, the implant 710 is releasably attached to the insertion instrument 500, the keels 736 are aligned with the keel channels, and the implant inserted into position. Thereafter the insertion instrument is detached from the implant 710 and removed from the patient.

Figure 39:
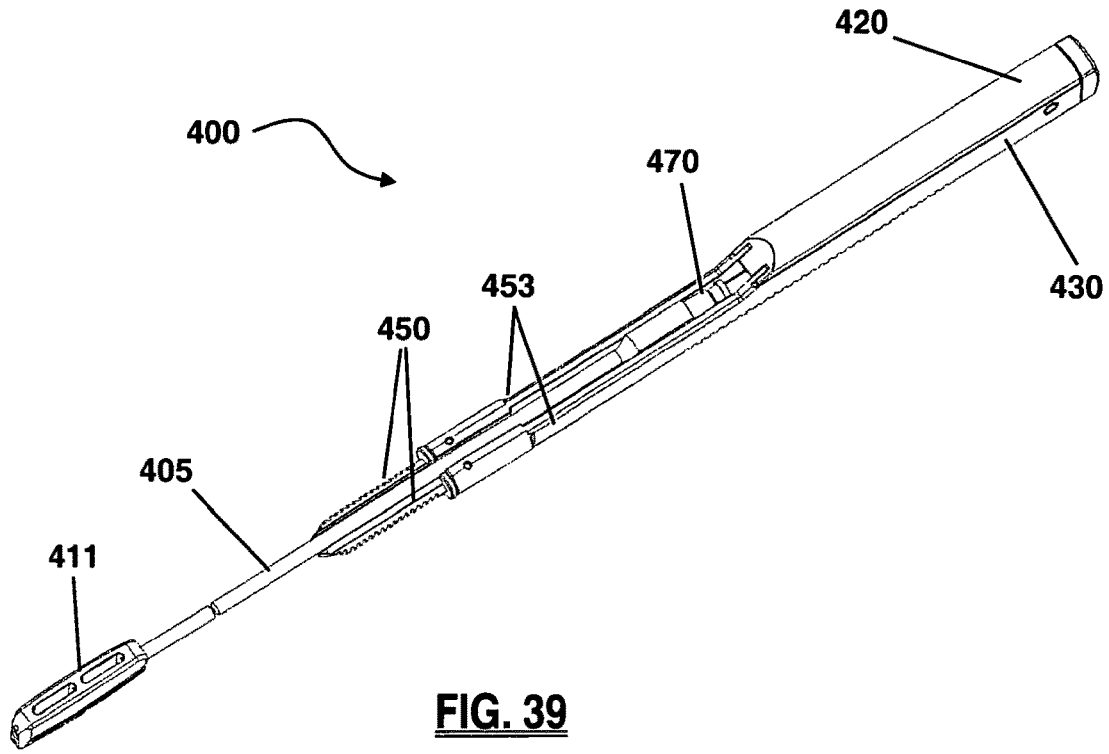
FIG. 39 is a perspective view of a keel cutter assembly, according to one embodiment of the present invention.
Figure 40:
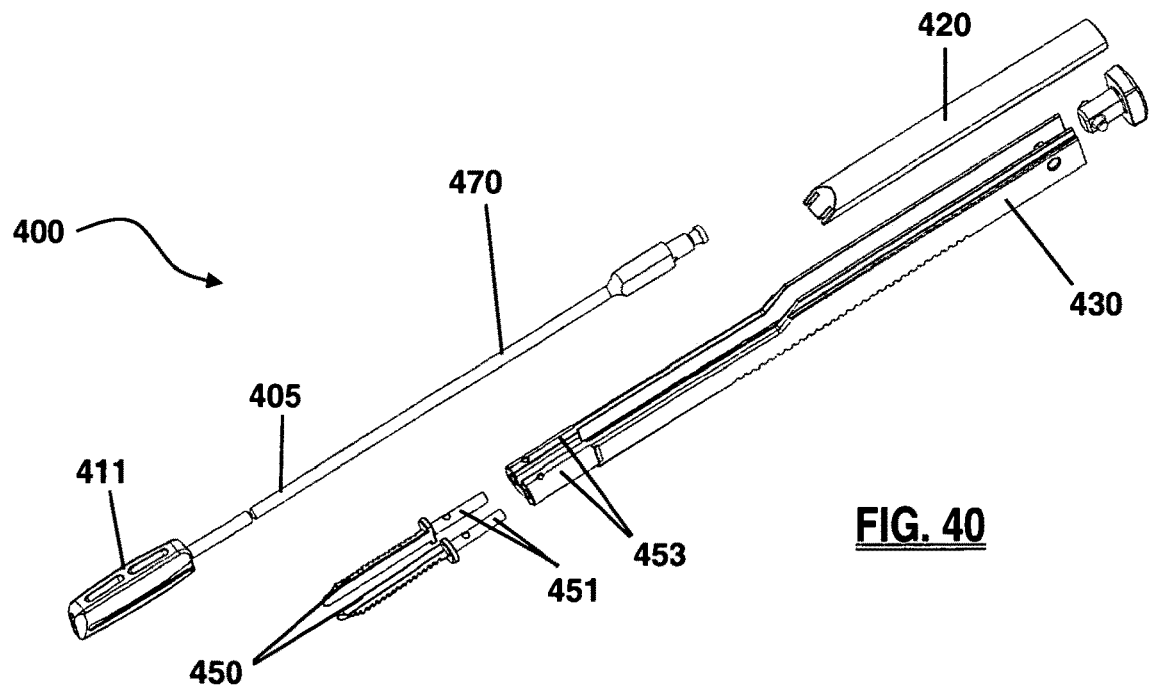
FIG. 40 is an exploded view of the keel cutter assembly of FIG. 39.
Figure 41:
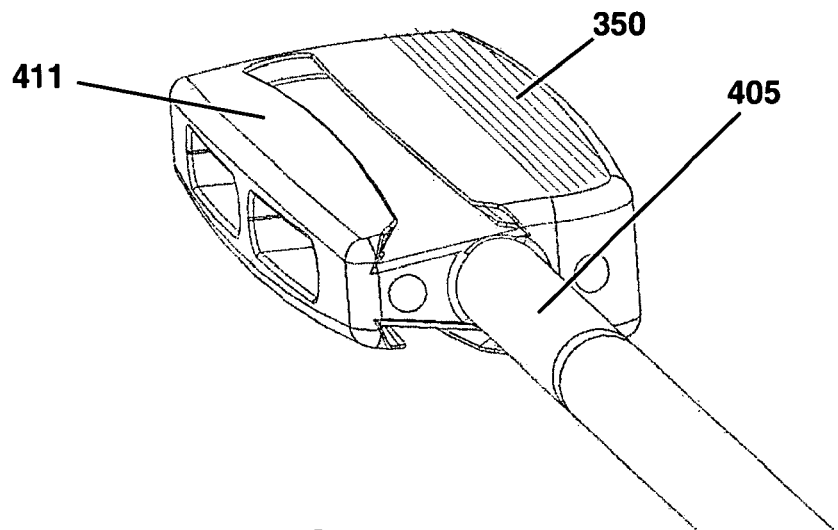
FIG. 41 is a perspective view of a trial sizer, according to one embodiment of the present invention.

FIGS. 39-42 illustrate a trial sizer and keel cutter instrument 400 according to one example embodiment. The trial sizer and keel cutter instrument 400 includes an inserter 470, an inserter holder 430, and keel channel blades 450. As illustrated in FIGS. 39-40, the inserter 470 includes an inserter shaft 405 that releasably attaches at its distal end to a trial sizer 411. A threadable attachment means is shown, but other means of releasable attachment are contemplated. As best illustrated in FIG. 39, the inserter shaft 405 fits within the width of the inserter holder 430 so that it can freely slide along the inserter holder 430. As shown in FIG. 41, the trial sizer 411 may have insertion grooves 350 along the sides that run generally parallel to the distal-proximal axis of the inserter 470. The insertion grooves help the trial sizer 411 travel in a straight path while the trial sizer 411 is being inserted into the intervertebral space.

For trial sizing, the trial sizer 411 is releasably attached to the inserter 470. The trial sizer 411 is progressed into the intervertebral space by sliding the inserter shaft 405 distally in relation to the inserter holder 430 until the trial sizer 411 is received into the intervertebral space. To remove the trial sizer 411, the inserter shaft 405 slides proximally in relation to the inserter holder 430 until the trial sizer 411 is free of the surgical corridor.

Figure 42A:
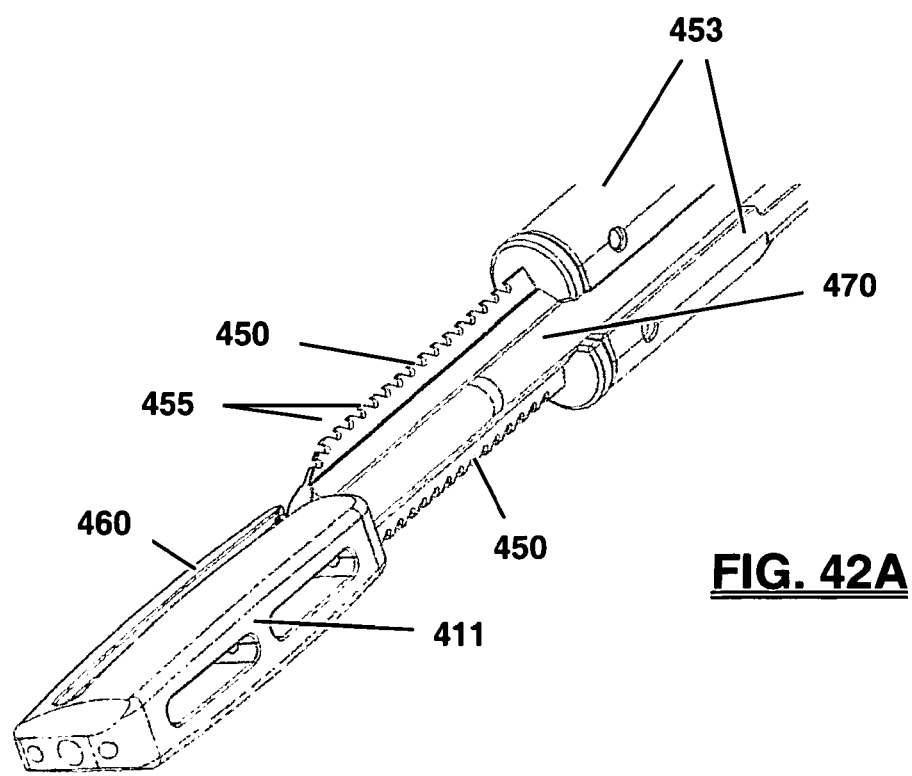
FIG. 42A-C are a series of perspective views of the blades of the keel channel cutter mating with the grooves of the trial sizer according to one embodiment of the present invention.
Figure 42B:
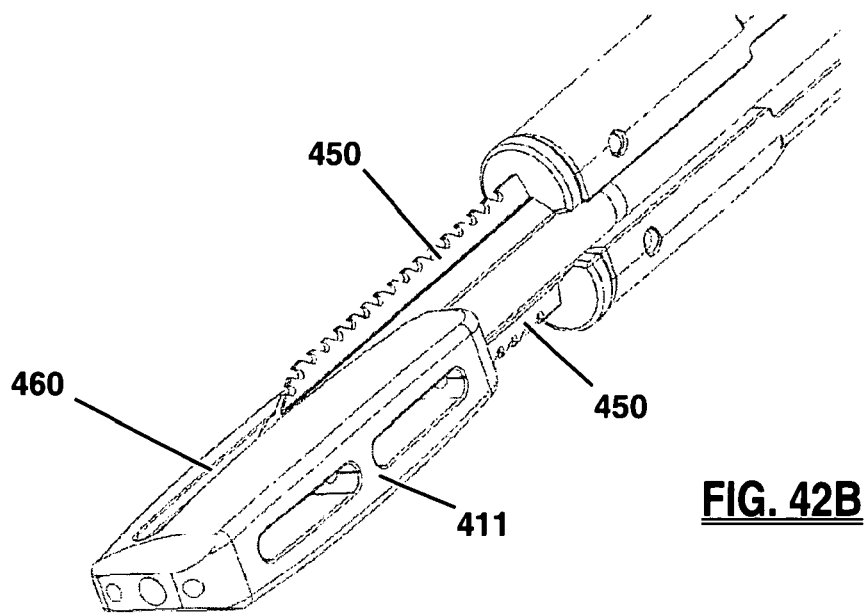
Figure 42C:
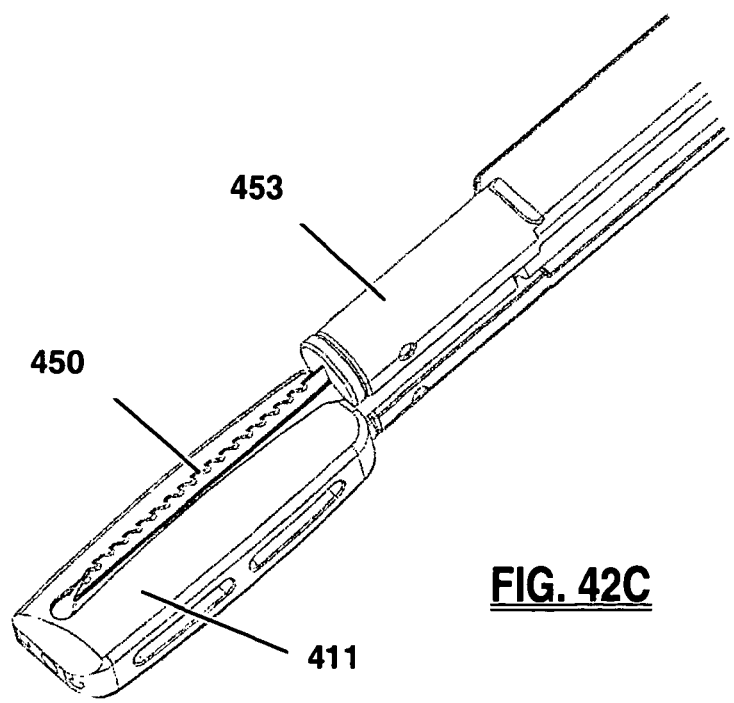

As illustrated in FIGS. 39-40, the inserter holder 430 includes a cover 420 that encloses a portion of the inserter shaft 405 by attaching to the inserter holder 430, providing the user with a handle. The distal end of the inserter holder 430 includes two blade holders 453, situated generally parallel to each other along the distal-proximal axis of the inserter holder 430. Two keel channel blades 450 attach to the blade holders 453 by handles 451 which insert into a channel (not shown) within the blade holder 453. As illustrated in FIG. 42A, the keel channel blades 450 attach to the blade holders 453 in a fixed orientation, so that the teeth 455 of the keel channel blades 450 point outwardly away from the trial sizer 411. The trial sizer 411 attaches to the inserter 470 in a fixed orientation, so that the keel channel blades 450 are able to slide across the trial sizer 411 and into keel channels 460 located on opposing outer surfaces of the trial sizer 411. As illustrated in FIGS. 42A-C, the keel channel blades 450 slide distally across the trial sizer 411 through the keel channels 460 to a final position spanning some portion of the trial sizer 411. When the trial sizer 411 is positioned within the intervertebral space, sliding the keel channel blades 450 distally from the inserter holder 430 so that the keel channel blades span a portion of the trial sizer 411 will cause the teeth 455 to cut a channel into the endplates or cancellous core of each vertebra. It should be appreciated that the keel channel blades may cut deeper or shallower channels into the adjacent vertebra to correspond to the size of the keels selected. When the channel is formed, the keel channel blades 450 can be removed by sliding the inserter 470 in a proximal direction until the keel channel blades 450 are clear of the trial sizer 411.

Figure 43:
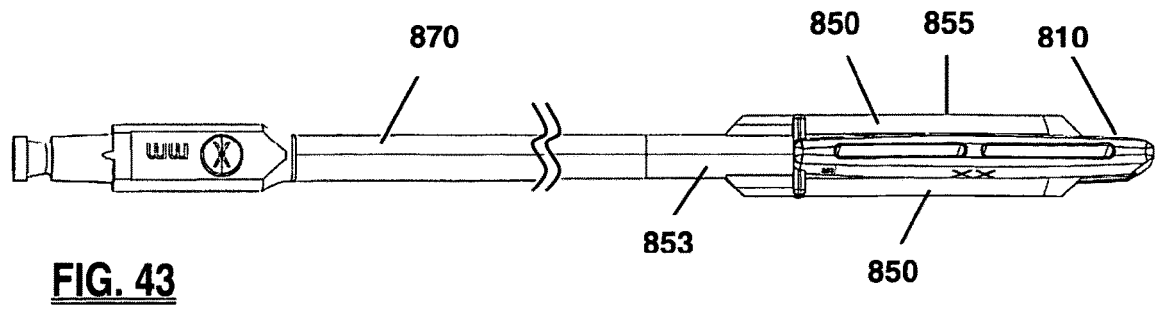
FIG. 43 is a side view of a keel cutter assembly and trial sizer, according to another embodiment of the present invention.
Figure 45:
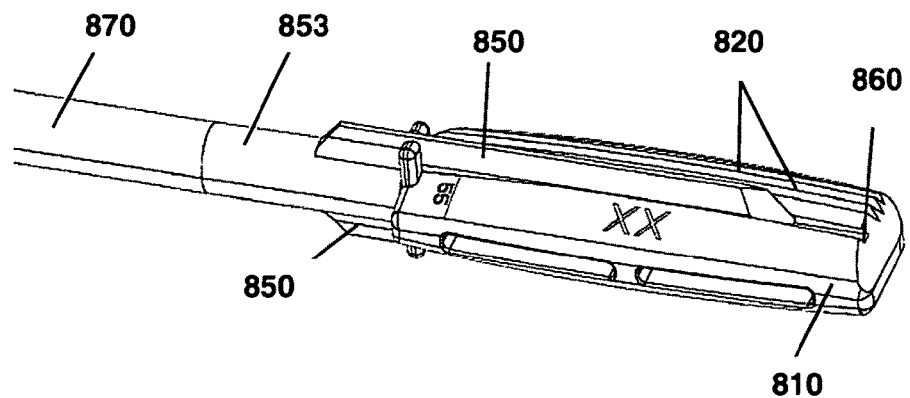
FIG. 45 is a perspective view of the blades of the keel channel cutter mating with the grooves of the trial sizer of FIG. 43.
Figure 46:
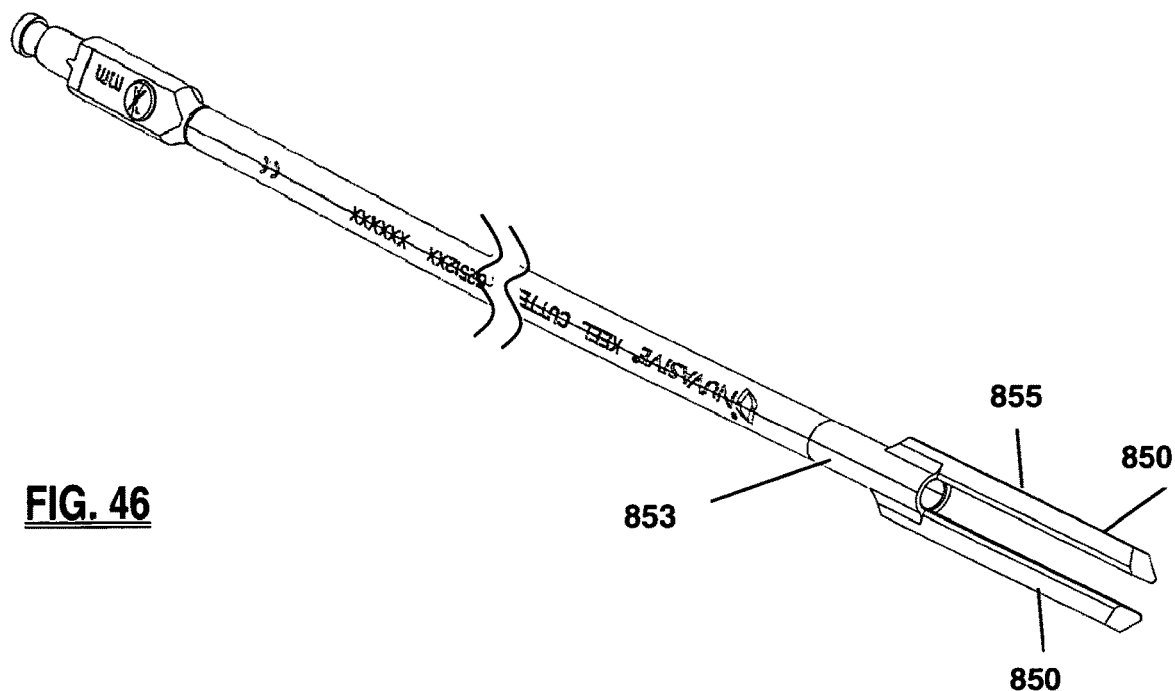
FIG. 46 is a perspective view of the inserter shaft and the blades of the keel channel cutter of FIG. 43.
Figure 47:
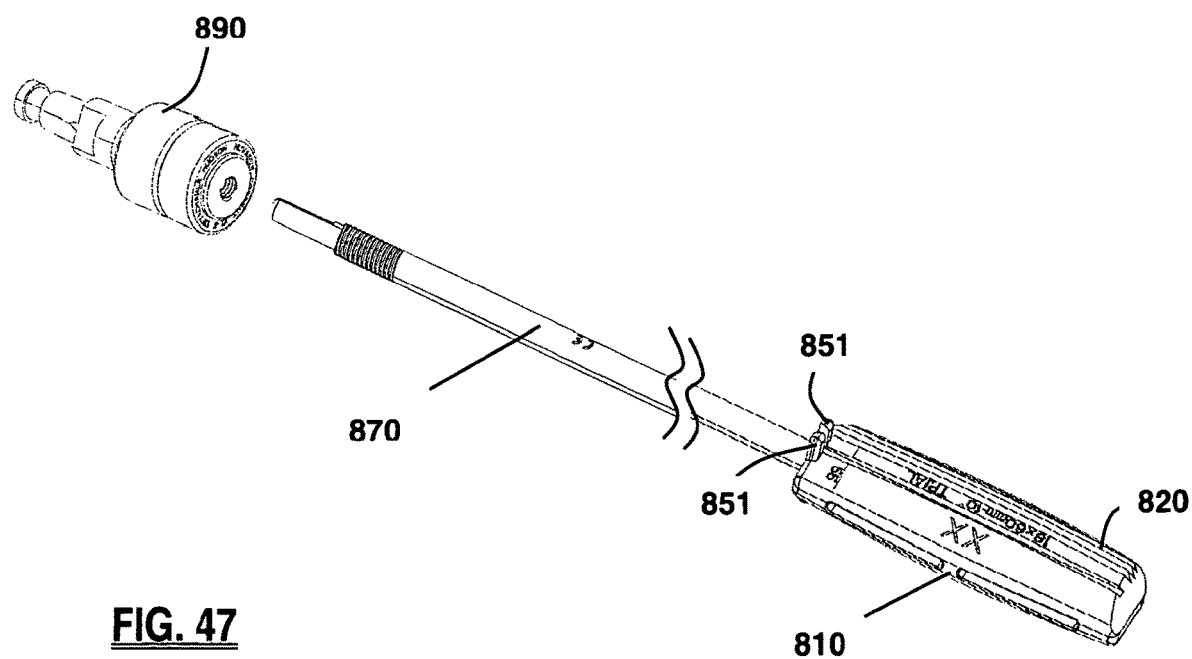
FIG. 47 is a perspective view of the trial sizer, inserter shaft of FIG. 43, together with a detachable Hudson connector forming part of the trial sizer, according to one embodiment of the present invention.

FIGS. 43-47 illustrate another example embodiment of a trial sizer and keel cutter assembly. As illustrated in FIG. 43, an inserter shaft 870 is releasably connected to a trial sizer 810. A threadable attachment or other means of releasable attachment between the trial sizer 810 and the inserter shaft 870 are contemplated. Alternatively, the inserter shaft 870 and sizer 810 may be permanently connected. Vertical extensions 851 at the proximal end of the sizer 810 will engage the faces of the upper and lower vertebra to prevent over insertion of the trial sizer (and keel cutter). As shown in FIG. 47, the trial sizer 810 may have insertion grooves 820 along the sides that run generally parallel to the distal-proximal axis of the inserter shaft 870. The insertion grooves 820 help the trial sizer 810 travel in a straight path while the trial sizer 810 is being inserted into the intervertebral space.

Figure 44:
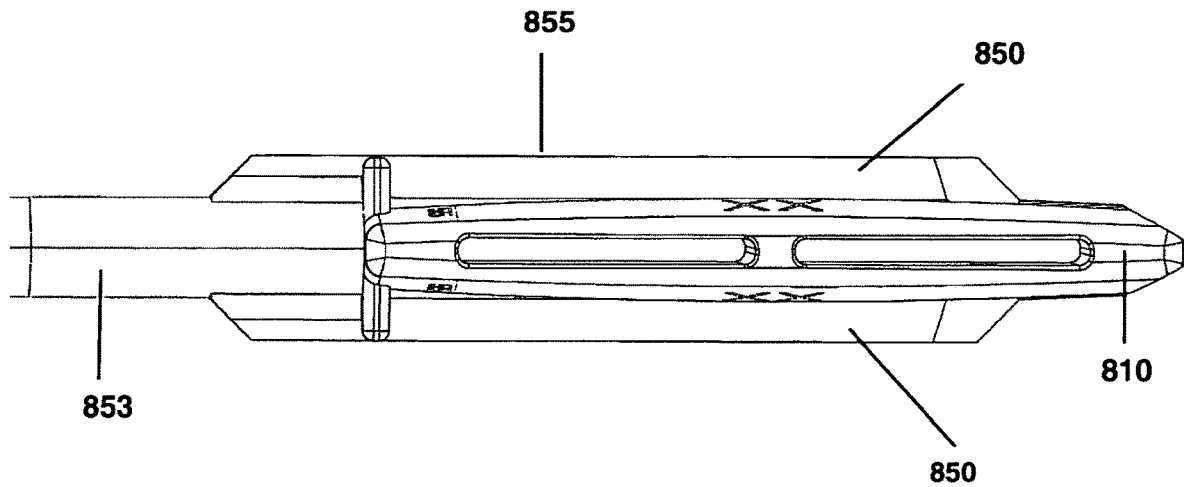
FIG. 44 is a side view of the blades of the keel channel cutter mating with the grooves of the trial sizer of FIG. 43.

As best illustrated in FIG. 46, two keel channel blades 850 are connected by a blade holder 853. Keel channel blades 850 may have ridged teeth (not shown). The keel channel blades 850 are connected to the blade holder 853 in a fixed orientation, so that the cutting edges 855 of the keel channel blades 850 point outwardly away from the trial sizer 810. The blade holder 853 comprises a cylindrical tube dimensioned to pass over the inserter shaft 870. As the blade holder 853 is advanced over the inserter shaft 870, the keel channel blades 850 slide across the trial sizer 810 and into blade channels 860 located on opposing outer surfaces of the trial sizer 810, as illustrated in FIG. 45. As illustrated in FIGS. 43-45, the keel channel blades 850 slide distally across the trial sizer 810 through the blade channels 860 to a final position spanning some portion of the trial sizer 810. When the trial sizer 810 is positioned within the intervertebral space, sliding the keel channel blades 850 distally along the inserter shaft and into the insertion grooves 820 will cause the keel channel blades 850 to cut a channel into the endplates or cancellous core of each adjacent vertebra. It should be appreciated that the keel channel blades 850 may cut deeper or shallower channels into the adjacent vertebra to correspond to the size of the keels selected. When the channel is formed, the keel channel blades 450 can be removed by sliding the blade holder 853 in a proximal direction until the keel channel blades 450 are clear of the intervertebral space. The inserter shaft includes a connector 890 for releasably attaching various handles or other instruments (e.g. T-handles, gear-shift handles, etc.) to aid in manipulating the trial sizer during insertion and removal. By way of example, the connector 890 is a Hudson connector. The connector 890 is preferably detachable, allowing the keel cutter to slide over the inserter shaft. According to this example, the inserter shaft includes threading on the distal end that engages interior threading on the Hudson connector.

Figure 48:
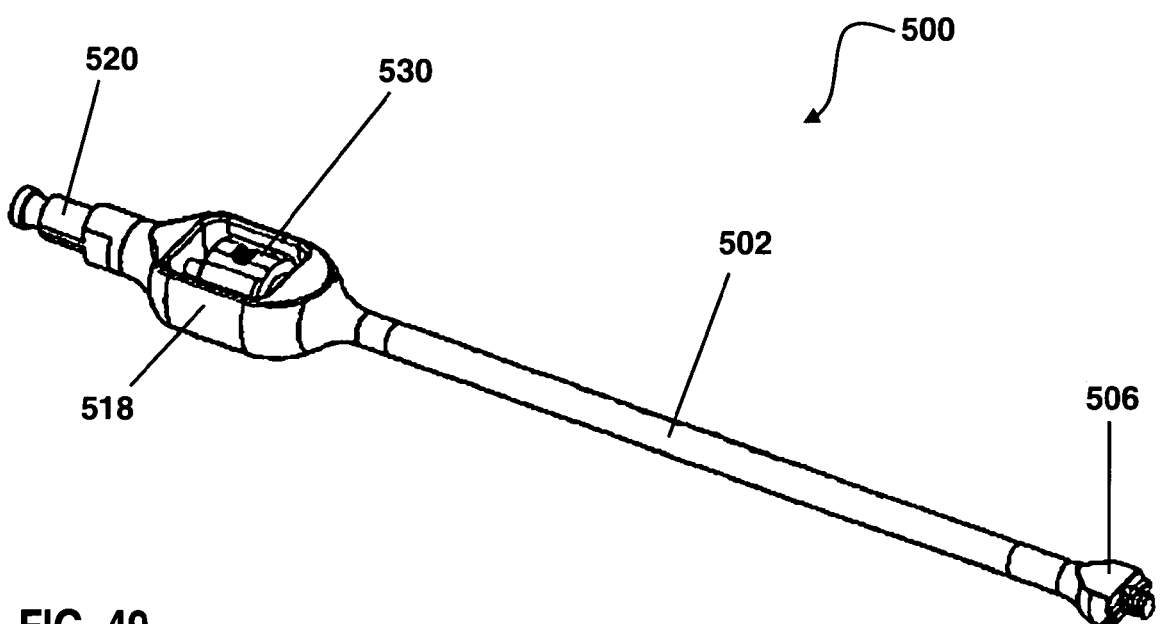
FIG. 48 is a perspective view of the insertion instrument according to one embodiment of the present invention.

FIGS. 48-50 detail an insertion instrument 500 according to one example embodiment of the present invention. The insertion instrument 500 includes an elongate tubular element 502 and an inserter shaft 504. The elongate tubular element 502 is constructed with a distal head 506 at its distal end, distal head ridges 508 on the distal end of the distal head 506, a thumbwheel housing 518 near its proximal end, a thumbwheel 530 within the thumbwheel housing 518, and a handle 520 at its proximal end. The elongate tubular element 502 is generally cylindrical and of a length sufficient to allow the device to span from the surgical target site to a location sufficiently outside the patient's body so that the handle 520 and thumbwheel housing 518 can be easily accessed by a clinician or a complimentary controlling device.

The elongate tubular element 502 is dimensioned to receive a spring 524 and the proximal end of the inserter shaft 504 into the inner bore (not shown) of the elongate tubular element 502. The inserter shaft 504 is dimensioned such that the threaded connector 522 at the distal end of the inserter shaft 504 protrudes from the inner bore, past the distal head ridges 508 to allow engagement with, by way of example only, the receiving aperture 148 of the spinal fusion implant 110 or trial sizer. It should be appreciated by one skilled in the art that such a construction allows the inserter shaft 504 to be able to rotate freely within the elongate tubular element 502 while stabilized by a spring 524 to reduce any slidable play in the insertion instrument 500. The distal head ridges 508 are dimensioned to fit slidably into the purchase regions 150 with low friction to allow accurate engagement of the threaded connector 522 to the receiving aperture 148 of the spinal fusion implant 110 or trial sizer. In the presented embodiment, the outer dimension of the threaded connector 522 is smaller than the largest outer dimension of the distal head 506 and elongate tubular element 502. Alternatively, other methods of creating a gripping surface are contemplated including but not limited to knurling or facets.

As illustrated in FIG. 50, the handle 520 is generally disposed at the proximal end of the insertion instrument 500. The handle 520 is fixed to the thumbwheel housing 518 allowing easy handling by the clinician. Because the handle 520 is fixed, the clinician has easy access to the thumbwheel 530 and can stably turn the thumbwheel 530 relative to the thumbwheel housing 518. Additionally, the relative orientation of the thumbwheel housing 518 to the distal head 506 orients the clinician with respect to the distal head 506 and an attached implant (not shown). By way of example, the thumbwheel housing 518 holds a thumbwheel 530 a set screw 532 and a spacer 534. The inserter shaft 504 is attached to the thumbwheel 530 and is freely rotatable with low friction due to the spacer 534. One skilled in the art can appreciate myriad methods of assembling a housing similar to the above described.

Figure 51:
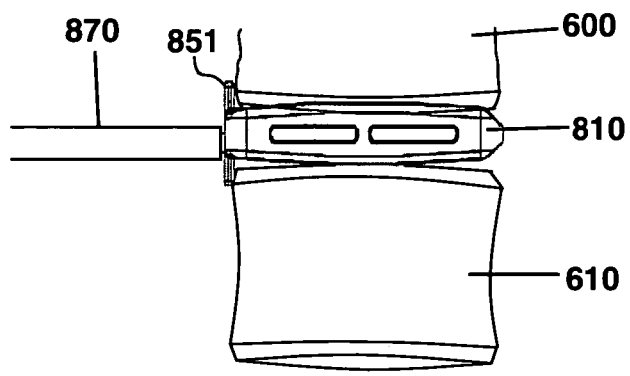
FIGS. 51-53 are a series of figures depicting the operation of a keel channel cutter according to one embodiment of the present invention.
Figure 52:
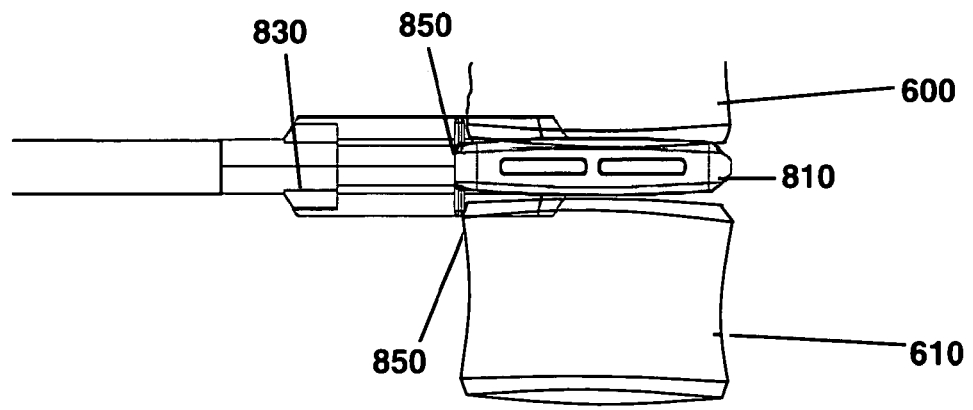
Figure 53:
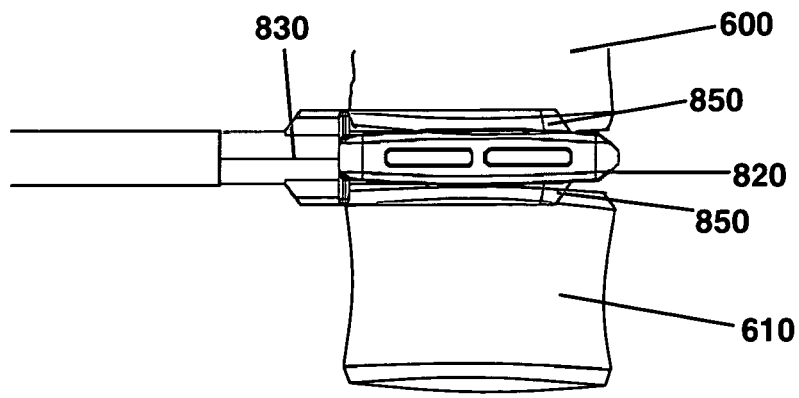
Figure 54:
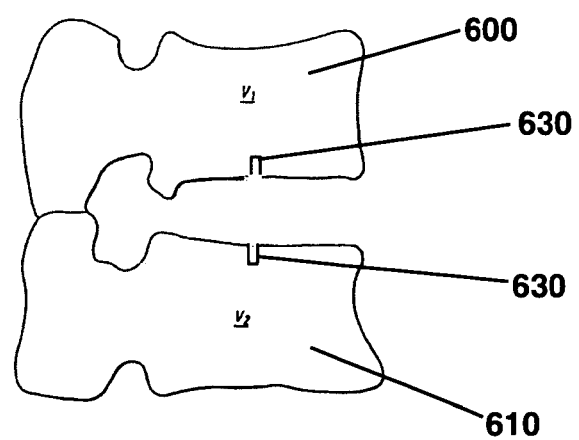
FIG. 54 is a side view of the intervertebral space containing keel channels formed by the operation of the keel channel cutter in FIGS. 51-53.

A clinician can utilize the secured implant in either an open or minimally invasive spinal fusion procedure. In either type of procedure, a surgical corridor is created in a patient that reaches the targeted spinal level. After the creation of that corridor, the intervertebral space may be prepared via any number of well known preparation tools, including but not limited to kerrisons, rongeurs, pituitaries, and rasps. Alternatively, if the intervertebral space already contains an implant to be replaced, that implant will be removed. After preparation, various trial sizers may be temporarily placed in the intervertebral space to determine the appropriate size of the final implant. With the appropriate trial sizer in place, keel channels 630 may be cut into the endplates or beyond the endplates into the cancellous bone of the adjacent vertebrae as needed to accommodate the desired keel structures 36. First, the trial sizer is inserted into the disc space, as in FIG. 51. When the appropriate size is determined, the trial sizer 810 remains positioned in the disc space between a top vertebra 600 and a bottom vertebra 610. The keel channel blades 850 are moved distally toward the vertebrae. The keel channel blades 850 advance into the intervertebral space above and below the trial sizer 810, cutting a groove into each vertebra corresponding to the approximate dimensions of the keel structures. The trial sizer 810 and keel channel blades 850 are then removed from the intervertebral space. FIG. 54 illustrates the keel channels 630 left in the upper and lower vertebral bodies when the trial sizer and keel cutter have been removed. The implant may then be attached to the insertion instrument 500, as described above, and advanced to the disc space with the keel structures aligned with the keel channels.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An implant for spinal fusion, the implant comprising:
a body comprising a top surface, a bottom surface, a distal side, a proximal side, a first side wall, a second side wall, and a fusion aperture that extends between the top and bottom surfaces,
the body further including an upper guide path on the top surface and
an upper penetration structure configured to couple with the upper guide path and extend above the top surface, wherein the upper penetration structure extends beyond the proximal side of the implant, and
wherein the upper penetration structure comprises a flexible tab configured to engage the body to lock the upper penetration structure to the body of the implant.

2. The implant of claim 1, wherein the upper guide path is parallel to a centerline of the body.

3. The implant of claim 1, wherein the upper penetration structure extends at least partly into the fusion aperture when coupled with the upper guide path.

4. The implant of claim 1, wherein the body further comprises a lower guide path on the bottom surface.

5. The implant of claim 4, further comprising a lower penetration structure configured to couple with the lower guide path and extend beyond the bottom surface, wherein the lower penetration structure extends beyond the proximal side of the implant.

6. The implant of claim 5, wherein the upper penetration structure and the lower penetration structure are made from a material different than that of the body of the implant.

7. The implant of claim 1, further comprising at least one side aperture extending through the first sidewall into the fusion aperture.

8. The implant of claim 1, wherein the first sidewall has a height dimension greater than that of the second sidewall.

9. The implant of claim 1, further comprising anti-migration features comprising one of angled ridges formed along the top surface, angled ridges formed along the bottom surface, or one or more spike members disposed along the body.

10. The implant of claim 1, wherein the flexible tab is configured to snap around the proximal side of the body.

11. The implant of claim 1, wherein the first sidewall defines an anterior side when said implant is positioned within an interbody space, and the second side wall defines a posterior side when the implant is positioned within the interbody space.

12. An implant for spinal fusion, the implant comprising:
a body comprising a top surface, a bottom surface, a distal side, a proximal side, a first side wall, a second side wall, and a fusion aperture that extends between the top and bottom surfaces,
the body further including an upper guide path on the top surface for matingly engaging an upper penetration structure and a lower guide path on the bottom surface for matingly engaging a lower penetration structure, wherein the upper penetration structure and the lower penetration structure are formed as a single component and coupled via a tapered end, and
wherein the upper penetration structure comprises a flexible tab configured to engage the body to lock the upper penetration structure to the body
wherein the first sidewall has a height dimension greater than that of the second sidewall.

13. The implant of claim 12, wherein the flexible tab extends beyond the distal side of the implant when the body of the implant is positioned within an interbody space.

14. The implant of claim 12, wherein the upper penetration structure extends at least partly into the fusion aperture when the upper penetration structure is coupled with the upper guide path.

15. The implant of claim 12, further comprising at least one side aperture extending through the first sidewall into the fusion aperture.

16. The implant of claim 12, further comprising one or more anti-migration features comprising angled ridges formed along the top surface, angled ridges formed along the bottom surface, or one or more spike members disposed along the body of the implant.

17. The implant of claim 12, wherein the upper penetration structure and the lower penetration structure are made from a material different than that of the body of the implant.

18. The implant of claim 12, wherein the flexible tab is configured to snap around the proximal side of the body of the implant.

* * * * *